United States Patent
Vidal et al.

(10) Patent No.: US 9,096,885 B2
(45) Date of Patent: Aug. 4, 2015

(54) METHOD AND APPARATUS FOR DETERMINING WHITE BLOOD CELL COUNTS

(71) Applicant: Beckman Coulter, Inc., Brea, CA (US)

(72) Inventors: Patricio Vidal, Miami, FL (US); Christophe Godefroy, Miramar, FL (US); Phaisit Chewputtanagul, Miami, FL (US); Jiuliu Lu, Homestead, FL (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/935,154

(22) Filed: Jul. 3, 2013

(65) Prior Publication Data

US 2014/0011232 A1     Jan. 9, 2014

Related U.S. Application Data

(60) Provisional application No. 61/668,377, filed on Jul. 5, 2012.

(51) Int. Cl.
*G01N 33/00*     (2006.01)
*G01N 31/00*     (2006.01)
(Continued)

(52) U.S. Cl.
CPC ...... *C12Q 1/06* (2013.01); *G01N 15/12* (2013.01); *G01N 15/1459* (2013.01); *G06F 19/345* (2013.01); *G01N 2015/008* (2013.01); *G01N 2015/0073* (2013.01); *G01N 2015/1006* (2013.01); *G01N 2015/1037* (2013.01);
(Continued)

(58) Field of Classification Search
CPC .......... G01N 2015/1037; G01N 15/1429; G01N 15/1459; G01N 2015/129; G01N 33/5094; G01N 15/12; G01N 15/147; G01N 33/537; G01N 15/1404; G01N 1/12; G01N 2015/0084; G01N 33/491; G01N 33/721; G01N 2015/0073; G01N 2015/008; G01N 2015/1006; G01N 2015/1402; G01N 2015/1413; G01N 2015/1486; G01N 2021/4707; G01N 2021/4769; G01N 21/53; C12Q 1/06; G06F 19/345
USPC .............................................. 422/73; 436/10
See application file for complete search history.

(56) References Cited

U.S. PATENT DOCUMENTS

| 5,125,737 A | 6/1992 | Rodriguez et al. |
| 5,616,501 A | 4/1997 | Rodriguez et al. |

(Continued)

FOREIGN PATENT DOCUMENTS

| WO | 2005-043113 A2 | 5/2005 |

OTHER PUBLICATIONS

Author Unknown, "Advancements in Technology: NRBC Enumeration," Beckman Coulter, 2009, 2 pages.

(Continued)

*Primary Examiner* — Dean Kwak
(74) *Attorney, Agent, or Firm* — Kilpatrick Townsend & Stockton LLP

(57) ABSTRACT

Embodiments of the present invention encompass automated systems and methods for analyzing white blood cell parameters in an individual based on a biological sample obtained from blood of the individual. Exemplary techniques involve correlating aspects of direct current (DC) impedance, radiofrequency (RF) conductivity, and/or light measurement data obtained from the biological sample with an evaluation of white blood cell conditions in the individual.

26 Claims, 22 Drawing Sheets

(51) Int. Cl.
  *C12Q 1/06* (2006.01)
  *G06F 19/00* (2011.01)
  *G01N 15/12* (2006.01)
  *G01N 15/00* (2006.01)
  *G01N 15/10* (2006.01)
  *G01N 15/14* (2006.01)

(52) U.S. Cl.
  CPC  *G01N2015/1402* (2013.01); *G01N 2015/1413* (2013.01); *G01N 2015/1486* (2013.01)

(56) References Cited

U.S. PATENT DOCUMENTS

| | | | |
|---|---|---|---|
| 5,656,499 A * | 8/1997 | Chupp et al. | 436/43 |
| 6,228,652 B1 | 5/2001 | Rodriguez et al. | |
| 6,744,245 B2 | 6/2004 | Taylor et al. | |
| 7,008,792 B2 | 3/2006 | Lopez et al. | |
| 7,208,319 B2 | 4/2007 | Lopez et al. | |
| 8,094,299 B2 | 1/2012 | Wells et al. | |
| 8,189,187 B2 | 5/2012 | Graham et al. | |
| 2004/0171164 A1 | 9/2004 | Li et al. | |
| 2007/0076190 A1 * | 4/2007 | Nakaya et al. | 356/39 |
| 2008/0098828 A1 | 5/2008 | Li et al. | |
| 2010/0075369 A1 | 3/2010 | Godefroy et al. | |
| 2010/0111400 A1 | 5/2010 | Ramirez et al. | |
| 2010/0228491 A1 | 9/2010 | Gutierrez et al. | |
| 2010/0240055 A1 | 9/2010 | Godefroy et al. | |

OTHER PUBLICATIONS

Author Unknown, "Advancements in Technology: Reticulocyte Methodology," Beckman Coulter, 2009, 2 pages.
Hedley, B., et al., "Initial Performance Evaluation of the Unicel® DxH 800 Coulter® Cellular Analysis System," International Journal of Laboratory Hematology, 2010, 12 pages.
International Search Report and Written Opinion of PCT/US2013/049367 mailed Nov. 7, 2013, 12 pages.

* cited by examiner

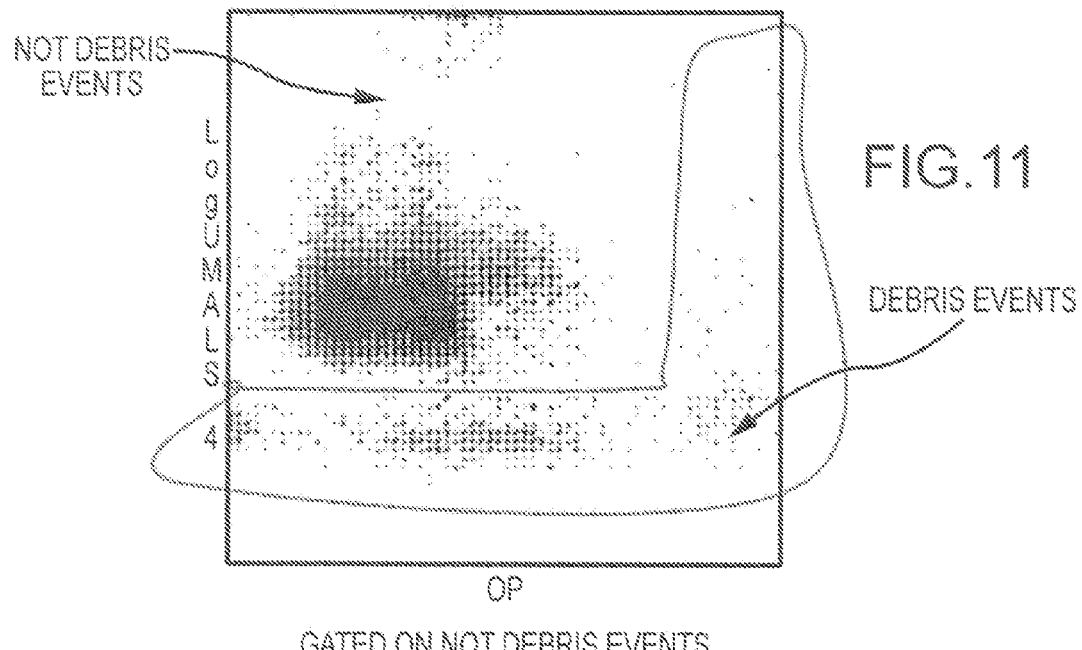

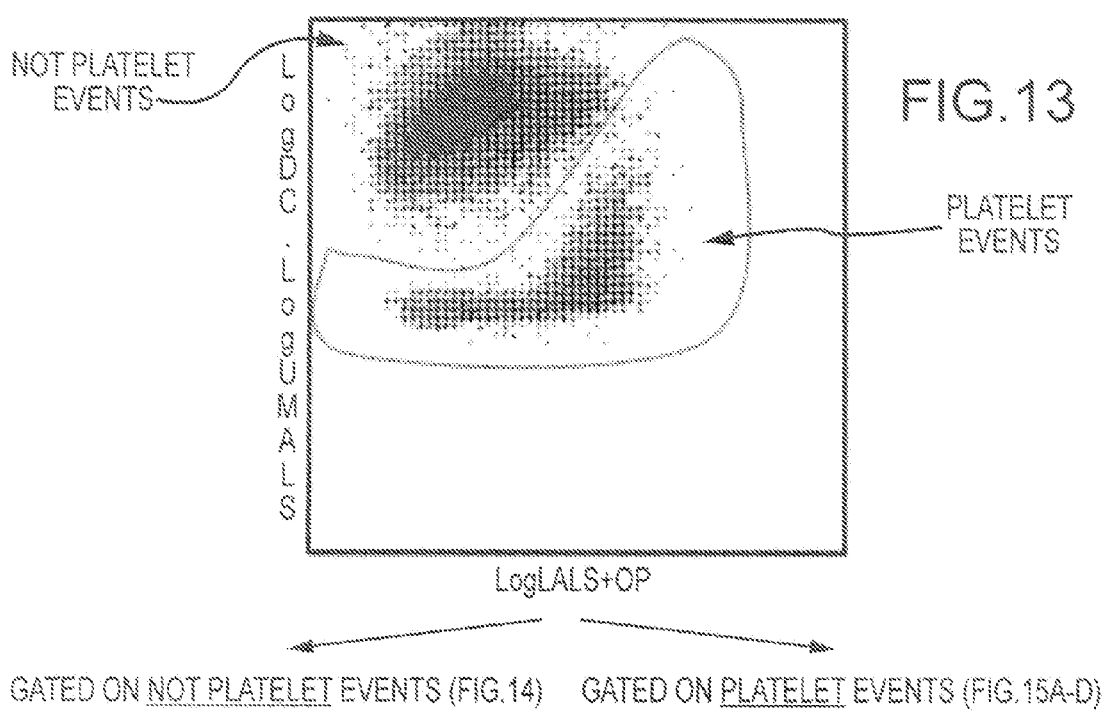
GATED ON NOT PLATELET EVENTS (FIG.14)   GATED ON PLATELET EVENTS (FIG.15A-D)
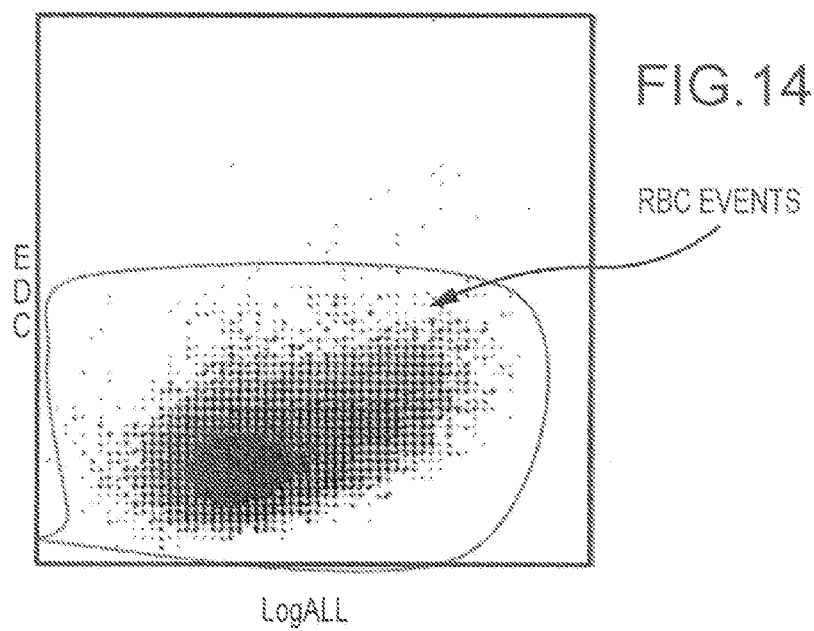

METHOD AND APPARATUS FOR DETERMINING WHITE BLOOD CELL COUNTS

CROSS-REFERENCES TO RELATED APPLICATIONS

This application claims the benefit of priority to U.S. Provisional Patent Application No. 61/668,377 filed Jul. 5, 2012. This application is also related to U.S. Pat. No. 6,744,245. The content of each of the above filings is incorporated herein by reference.

BACKGROUND OF THE INVENTION

Embodiments of the invention relate generally to the field of medical diagnostics and more specifically encompass methods and devices for producing a white blood cell (WBC) count without the need for lysing the red blood cells (RBCs) and without the need for coincidence correction.

A common medical test that is used for the determination of a patient's health is the complete blood count (CBC) which determines the number of various types of blood cells per unit volume of the patient's blood. One type of blood cell that is counted is the white blood cell.

White blood cells, known also as leukocytes, are cells released by the immune system to fight infection and respond to foreign matter in the body. There are many types of white blood cells, including neutrophils; eosinophils; basophils; lymphocytes and monocytes. These cells are generally named according to the types of stains that they absorb.

In a healthy adult, white blood cells make up about 1% of the blood cells which corresponds to $4 \times 10^3$ to $1 \times 10^4$ cells per microliter of blood. Deviations from this range may indicate a disease state. Some diseases, such as leukemia or infections, result in leukocytosis, a rising of the white blood cell count. Some diseases result in leucopenia a lowering of the white blood cell count. These diseases include viral infections or bone marrow disorders.

Another blood cell type is the reticulocyte. A reticulocyte is an immature red blood cell. Reticulocytes include a reticulum of ribonucleic acid (RNA) which is lost as the cells mature into red blood cells. Typically reticulocytes are 0.5%-1.5% of the red blood cells in the adult body. The number of reticulocytes may increase as a result of blood loss, for example in injury, or red blood cell destruction, for example, in certain types of anemia. Low reticulocyte counts may be the result of other types of anemia, exposure to radiation, or certain medicines which affect the bone marrow.

Exemplary present day hematological analyzers utilize flow cells to count and characterize blood samples. These devices include a number of specimen processing modules which are programs used to selectively identify the blood cells in the sample. For example a reticulocyte module permits red blood cells and reticulocytes to be counted.

However, a problem in obtaining an accurate WBC count can occur when the patient's white blood cell count is significantly elevated. In these cases the impedance based WBC count module that the hematological analyzer typically uses has trouble directly distinguishing individual white blood cells because of coincidence. Coincidence issues arise when the concentration of a cell type is high enough that the analyzer cannot distinguish the individual cells and counts two or more cells as one. Coincidence correction affects all WBC counts but with higher impact for increased concentrations of WBCs. Without correction the result is that the white blood cell concentration may be underreported. Existing approaches attempt to correct for these issues algorithmically to adjust for coincidence.

Hence, although WBC count systems and methods are currently available and provide real benefits to patients in need thereof, many advances may still be made to provide improved devices and methods for assessing the status of WBCs in an individual. Embodiments of the present invention provide solutions that address these problems, and hence provide answers to at least some of these outstanding needs.

BRIEF SUMMARY OF THE INVENTION

Embodiments of the present invention provide improved techniques for analyzing white blood cell conditions or parameters in an individual. Such techniques can employ various combinations of Complete Blood Cell Count (CBC) parameters in addition to Volume Conductivity Scatter (VCS) parameters, so as to provide reliable screening approaches that assess WBC conditions of patients or individuals in the general population. For example, diagnostic systems and methods can provide an early and accurate prediction as to whether an individual has normal or abnormal WBC counts or parameters. Such WBC analysis techniques may involve calculating certain RBC measures using a reticulocyte module of a hematology analyzer.

Blood samples from patients who come under the care of a physician can be evaluated using a hematology system that is equipped to obtain multiple light angle detection parameters, such as Beckman Coulter's UniCel® DxH™ 800 Cellular Analysis System. By employing the techniques disclosed herein, hematopathologists and clinicians can better predict disease prognosis for each individual patient, assess the likelihood of future complications, and quickly and accurately tailor the therapy offered to patients.

The DxH 800 hematology analyzer is able to directly recognize morphologic features indicative of types of blood components such as white blood cells, red blood cells, and platelets. As discussed elsewhere herein, this technology simultaneously collects data on various parameters that are directly correlated to cellular morphology or certain cellular events. As cellular components are analyzed, they can be plotted in histograms with their position being defined by various parameters. For example, since different blood cell types may have different features, they can be plotted or segmented in different regions of the histogram, thus forming cell populations. The number of events in each population can be used to generate a count. Besides such counts, the mean and standard deviation values for the points of each of various morphologic parameters (volume, conductivity, and five angles of light scatter) can be calculated separately. As a result, a vast amount of data directly correlating to cellular events is generated. This information can be referred to as VCS data, and it can be viewed on the screen of the instrument, as well as automatically exported as an Excel file. Embodiments of the present invention may include evaluating a biological sample from an individual by obtaining a profile for the biological sample that involves VCS data, optionally in combination with CBC data, and assigning a WBC parameter such as a WBC count or value to the biological sample based on the data. Certain embodiments may also include outputting the WBC count. One or more of these steps may be performed by a hematology analyzer such as Beckman Coulter's UniCel® DxH™ 800 Cellular Analysis System.

Embodiments of the present invention provide quick and accurate WBC screening results. Using the approaches disclosed herein, it is possible to evaluate and predict a WBC condition in an individual, using information obtained from a multi-parametric cellular analysis system. As disclosed herein, exemplary cellular analysis systems can simultaneously measure parameters such as volume, conductivity, and/or multiple angles of light scatter. Such systems provide a high degree of resolution and sensitivity for implementing cellular analysis techniques. In some instances, cellular analysis systems detect light scatter at three, four, five, or more angular ranges. Additionally, cellular analysis systems also can detect signals at an angle between 0° to about 1° from the incident light, which corresponds to a light extinction parameter known as axial light loss. As a non-limiting example, Beckman Coulter's UniCel® DxH™ 800 Cellular Analysis System provides light scatter detection data for multiple angles (e.g. between 0°-0.5° for AL2, about 5.1° for LALS, between 9°-19° for LMALS, and between 20°-43° for UMALS). These techniques allow for fast, accurate diagnosis and treatment of patients having abnormal WBC parameters, particularly in situations where more modern tests are not readily available.

Such hematology analysis instruments can evaluate more than 8,000 cells in a matter of seconds, and the morphologic features of cellular volume, cytoplasmic granularity, nuclear complexity, and internal density can be evaluated quantitatively. Numerical decision rules can be generated and used to implement strategies for predicting a WBC condition state or status in an individual. For example, a WBC condition state or status may be associated with a WBC count for the individual. In some instances, the WBC condition or state may refer to a calculated WBC count for the individual.

Hence, embodiments of the present invention encompass systems and methods for the diagnosis or monitoring of WBC associated conditions using multiparametric models for disease classification. Patterns of morphological change can be analyzed by combining information from various measured parameters. Hence, embodiments of the present invention are well suited for use in analyzing WBC parameters for evaluating blood disorders like leukemia, and for monitoring the course and treatment of conditions associated with elevated or depressed white blood cell counts. WBC analysis systems and methods as disclosed herein can be used to provide indicators of treatment progress in patients treated for leukemia, infections (e.g. viral infections), and bone marrow disorders.

Exemplary techniques as disclosed herein encompass methods and systems for producing a correct white blood cell count without the need for lysing the red blood cells and without the need for a coincidence correction. In one aspect, embodiments of the present invention relate to a method for measuring white blood cell count using a reticulocyte module of a hematology analyzer when the white blood cell count is high. In one embodiment the method includes steps of: exposing the blood sample to light in a hematological analyzer; measuring the amount of scatter at a plurality of scattering angles using the hematological analyzer; calculating the amount of scatter at predefined ones of the plurality of scattering angles using a computer; determining, using an algorithm, executed by a computer, a population of red blood cells (mature red blood cells and reticulocytes) separated from a population of white blood cells; determining, using a computer, a count of reticulocytes and white blood cells in response to the separation. In one embodiment the WBC distinguished population may include but does not have to include nucleated red blood cells.

In yet another embodiment the predefined ones of the plurality of scattering angles comprise ALL, LALS, and MALS.

In still yet another embodiment the step of calculating the amount of scatter at predefined ones of the plurality of scattering angles comprises calculating the log of LALS. In one embodiment the step of calculating the amount of scatter at predefined ones of the plurality of scattering angles comprises calculating sum of the log of LALS and the log of MALS. In another embodiment the transparency of the cell is measured by ALL. In still yet another embodiment the step of counting the amount of WBCs comprises calculating the relationship: $UWBC\#_{Retic}=RBC\#_{CBC} \times ((WBC\&NRBC)_{events\ Retic}/RBC_{events\ Retic})$ In one embodiment the step determining the amount of WBCs comprises calculating the relationship: $UWBC\#_{Retic}=URBC\#_{CBC} \times (WBC\&NRBC_{events\ Retic}/(RBC_{eventts\ Retic}+(WBC\&NRBC)_{events\ Retic}))$ In another embodiment the method further comprises the step of correcting the WBC count by using the NRBC% from the NRBC module according the relationship: $WBC\#_{Retic}=UWBC\#_{Retic}/(1+NRBC\%_{NRBC})$. In another embodiment, where the WBC population does not include NRBCs the step of counting the amount of WBCs comprises calculating the relationship: $WBC\#_{Retic}=RBC\#_{CBC} \times (WBC_{events\ Retic}/RBC_{events\ Retic})$.

In another aspect, embodiments of the present invention relate to an apparatus for counting white blood cells using a reticulocyte module. In one embodiment the apparatus includes a hematological analyzer. In another embodiment the hematological analyzer includes a light source, the light source irradiating the blood sample with light in the hematological analyzer; and a detector array, the detector array measuring the amount of light scatter at a plurality of scattering angles; and a processor in electrical communication to the detector array, the processor connected to the detector array of the hematological analyzer, the computer calculating the log of the amount of scatter at predefined ones of the plurality of scattering angles; the processor determining, using a clustering algorithm, a population of the red blood cells (mature red blood cells and reticulocytes) separated from a population of white blood cells; the processor determining the amount of reticulocytes and white blood cells in response to the separation.

In one embodiment of the apparatus, the predefined ones of the plurality of scattering angles comprise ALL, LALS, and MALS. In yet another embodiment a processor, calculating the amount of scatter at predefined ones of the plurality of scattering angles, calculates the log of LALS. In still yet another embodiment the processor calculates the amount of scatter at predefined ones of the plurality of scattering angles comprises calculating sum of the log of LALS and the log of MALS. In one embodiment the volume is measured by ALL. In another embodiment the processor counting the amount of WBCs calculates the relationship: $UWBC\#_{Retic}=RBC\#_{CBC} \times (WBC\&NRBC_{events\ Retic}/RBC_{events\ Retic})$ In another embodiment the processor counting the amount of WBCs calculates the relationship: $UWBC\#_{Retic}=URBC\#_{CBC} \times (WBC\&NRBC_{events\ Retic}/(RBC_{events\ Retic}+WBC\&NRBC_{events\ Retic}))$ In still yet another embodiment the processor counting the amount of WBCs corrects the WBC count by using the NRBC % from the NRBC module according the relationship: $WBC\#_{Retic}=UWBC\#/(1+NRBC\%_{NRBC})$ In another embodiment, where the WBC population does not include NRBCs the step of counting the amount of WBCs comprises calculating the relationship: $WBC\#_{Retic}=RBC\#_{CBC} \times (WBC_{events\ Retic}/RBC_{events\ Retic})$.

In one aspect, embodiments of the present invention encompass automated systems and methods for estimating a white blood cell status in an individual based on a biological sample obtained from blood of the individual. Exemplary systems may include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. In some cases, the light detection assembly configured to measure a first propagated light from the irradiated cells within a first range of relative to the light beam axis, a second propagated light from the irradiated cells within a second range of angles relative to the light beam axis, the second range being different than the first range, and an axial light propagated from the irradiated cells along the beam axis. In certain embodiments, the system is configured to correlate a subset of DC impedance, the first propagated light, the second propagated light, and the axial light measurements from the cells of the biological sample with an estimation of an white blood cell status in the individual. According to some embodiments, the estimation of the white blood cell status of the individual includes an estimation of a white blood cell count. In certain instances, the DC impedance measurement is obtained via a reticulocyte module, and the system is configured to correlate the DC impedance measurement with the estimation of the white blood cell status of the individual. Optionally, a light measurement of the subset can be obtained via a reticulocyte module, and the system can be configured to correlate the light measurement obtained via the reticulocyte module with the estimation of the white blood cell status of the individual. In some cases, a light measurement of the subset can be obtained via a reticulocyte module, the DC impedance measurement can also be obtained via the reticulocyte module, and the system can be configured to correlate the DC impedance measurement obtained via the reticulocyte module, the light measurement obtained via the reticulocyte module, and a red blood cell count obtained via a Complete Blood Cell Count module with the estimation of the white blood cell status of the individual. In some cases, the system includes the Complete Blood Cell Count module. In some cases, a light measurement of the subset which is obtained via the reticulocyte module can include a lower angle light scatter (LALS) measurement, a lower median angle light scatter (LMALS) measurement, an upper median angle light scatter (UMALS) measurement, or an axial light loss (ALL) measurement. In some cases, the biological sample is a blood sample of the individual. In some cases, a light measurement of the subset is obtained via a reticulocyte module, a DC impedance measurement is obtained via the reticulocyte module, and the system is configured to correlate the DC impedance measurement obtained via the reticulocyte module, the light measurement obtained via the reticulocyte module, a red blood cell count obtained via a Complete Blood Cell Count module, and a nucleated red blood cell (NRBC) parameter obtained via an NRBC module, with the estimation of the white blood cell status of the individual.

In another aspect, embodiments of the present invention encompass systems and methods for estimating a white blood cell status in an individual based on a biological sample obtained from blood of the individual. Exemplary methods may include delivering a hydrodynamically focused stream of the biological sample toward a cell interrogation zone of an optical element, measuring, with an electrode assembly, current (DC) impedance of cells of the biological sample passing individually through the cell interrogation zone, irradiating, with an electromagnetic beam having an axis, cells of the biological sample individually passing through the cell interrogation zone, measuring, with a light detection assembly, a first propagated light from the irradiated cells within a first range of relative to the beam axis, measuring, with the light detection assembly, a second propagated light from the irradiated cells within a second range of angles relative to the beam axis, the second range being different than the first range, measuring, with the light detection assembly, axial light propagated from the irradiated cells along the beam axis, and correlating a subset of DC impedance, the first propagated light, the second propagated light, and the axial light measurements from the cells of the biological sample with an estimated white blood cell status of the individual.

In another aspect, embodiments of the present invention encompass methods of evaluating a biological sample from an individual that involve obtaining a current light propagation data profile for the biological sample, assigning a white blood cell status indication to the biological sample based on the current light propagation data profile, and outputting the assigned white blood cell status indication.

In another aspect, embodiments of the present invention encompass automated systems for estimating a white blood cell status of an individual based on a biological sample obtained from the individual. Exemplary systems include a conduit configured to receive and direct movement of the biological sample thorough an aperture, a light scatter and absorption measuring device configured to emit light through the biological sample as it moves through the aperture and collect data concerning scatter and absorption of the light, and a current measuring device configured to pass an electric current through the biological sample as it moves through the aperture and collect data concerning the electric current. In some cases, systems are configured to correlate the data concerning scatter and absorption of the light and the data concerning the electric current with an estimated white blood cell status of the individual.

In still another aspect, embodiments of the present invention encompass automated systems for estimating a white blood cell status of an individual based on a biological sample obtained from the individual. Exemplary systems include a transducer for obtaining light scatter data, light absorption data, and current data for the biological sample as the sample passes through an aperture, a processor, and a storage medium. In some instances, the storage medium has a computer application that, when executed by the processor, is configured to cause the system to use the light scatter data, the light absorption data, the current data, or a combination thereof, to determine an estimated white blood cell status of the individual, and to output from the processor information relating to the estimated white blood cell status.

In yet another aspect, embodiments of the present invention encompass automated systems for estimating a white blood cell status of an individual based on a biological sample obtained from the individual, where the systems include a transducer for obtaining current light propagation data for the biological sample as the sample passes through an aperture, a processor, and a storage medium. The storage medium may include a computer application that, when executed by the processor, is configured to cause the system to use the current light propagation data to determine an estimated white blood cell status of the individual, and to output from the processor information relating to the estimated white blood cell status.

In still another aspect, embodiments of the present invention include automated systems for identifying if an individual may have an abnormal white blood cell status based on a biological sample obtained from the individual. Exemplary systems may include a storage medium, a processor, and a transducer. The transducer can be configured to obtain light scatter data, light absorption data, and current data for the biological sample as the sample passes through an aperture. The storage medium may include a computer application that, when executed by the processor, is configured to cause the system to use a parameter, which is based on one or more measures of the light scatter data, light absorption data, or current data, to determine an estimated white blood cell status of the individual, and to output from the processor white blood cell information relating to the estimated white blood cell status of the individual.

In another aspect, embodiments of the present invention encompass systems and methods for evaluating a biological sample obtained from an individual. Exemplary methods may include passing the biological sample through an aperture of a particle analysis system, and obtaining light scatter data, light absorption data, and current data for the biological sample as the sample passes through the aperture. Exemplary methods may also include determining a current light propagation data profile for the biological sample based on the light scatter data, the light absorption data, the current data, or a combination thereof, and assigning a white blood cell status indication to the biological sample based on the current light propagation data profile. Exemplary methods may also include outputting the assigned white blood cell status indication.

In yet another aspect, embodiments of the present invention encompass automated methods for evaluating a biological sample from an individual. Exemplary methods include obtaining, using a particle analysis system, light scatter data, light absorption data, and current data for the biological sample as the sample passes through an aperture, and determining a current light propagation data profile for the biological sample based on assay results obtained from the particle analysis system. Exemplary methods may also include determining, using a computer system, an estimated white blood cell status for the individual according to a parameter, where the parameter is based on a current light propagation data measure of the current light propagation data profile. Exemplary methods may also include outputting the estimated white blood cell status.

In another aspect, embodiments of the present invention encompass automated systems for estimating a white blood cell status of an individual. Exemplary systems include a storage medium and a processor. The storage medium may include a computer application that, when executed by the processor, is configured to cause the system to access information concerning a biological sample of the individual. The information may include information relating at least in part to an axial light loss measurement of the sample, a light scatter measurement of the sample, a current measurement of the sample, or a combination of two or more thereof. The computer application may also, when executed by the processor, be configured to cause the system to use the information relating at least in part to the axial light loss measurement, the plurality of light scatter measurements, the current measurement, or the combination thereof, to determine an estimated white blood cell status of the individual. The computer application may also, when executed by the processor, be configured to cause the system to output from the processor information relating to the estimated white blood cell status. In some instances, the current measurement includes a low frequency current measurement of the sample. In some instances, the light scatter measurement includes a low angle light scatter measurement, a lower median angle light scatter measurement, an upper median angle light scatter measurement, or a combination of two or more thereof. In some cases, a system may include an electromagnetic beam source and a photosensor assembly. The photosensor assembly may be used to obtain the axial light loss measurement. In some instances, a system may include an electromagnetic beam source and a photosensor assembly, where the photosensor assembly is used to obtain the light scatter measurement. In some instances, a system may include an electromagnetic beam source and an electrode assembly, where the electrode assembly is used to obtain the current measurement.

In still another aspect, embodiments of the present invention encompass automated systems for estimating a white blood cell status of an individual. Exemplary systems may include a storage medium and a processor. The storage medium may include a computer application that, when executed by the processor, is configured to cause the system to access current light propagation data concerning a biological sample of the individual, to use the current light propagation data to determine an estimated white blood cell status of the individual, and to output from the processor information relating to the estimated white blood cell status. In some cases, the processor is configured to receive the current light propagation data as input. In some cases, the processor, the storage medium, or both, are incorporated within a hematology machine. In some cases, the hematology machine generates the current light propagation data. In some cases, the processor, the storage medium, or both, are incorporated within a computer, and the computer is in communication with a hematology machine. In some cases, the hematology machine generates the current light propagation data. In some cases, the processor, the storage medium, or both, are incorporated within a computer, and the computer is in remote communication with a hematology machine via a network. In some cases, the hematology machine generates the current light propagation data. In some cases, the current light propagation data includes an axial light loss measurement of the sample, a light scatter measurement of the sample, or a current measurement of the sample.

In another aspect, embodiments of the present invention encompass systems and methods for evaluating the physiological status of an individual. Exemplary systems may include a storage medium and a processor. The storage medium may include a computer application that, when executed by the processor, is configured to cause the system to access current light propagation data concerning a biological sample of the individual, and to use a parameter, which is based on a measure of the current light propagation data, to determine the physiological status of the individual. The determined physiological status can provide an indication whether the individual has a normal white blood cell status. The computer application may also, when executed by the processor, be configured to cause the system to output from the processor information relating to the physiological status of the individual.

In still yet another aspect, embodiments of the present invention encompass automated systems and methods for identifying if an individual may have an abnormal white blood cell status from hematology system data. Exemplary systems may include a storage medium and a processor. The storage medium may include a computer application that, when executed by the processor, is configured to cause the system to access hematology current light propagation data concerning a blood sample of the individual, and to use a parameter, which is based on a measure of the hematology current light propagation data, to determine an estimated white blood cell status of the individual. The computer application may also, when executed by the processor, be configured to cause the system to output from the processor white blood cell information relating to the estimated white blood cell status of the individual.

In a further aspect, embodiments of the present invention encompass automated systems and methods for evaluating a biological sample from an individual. Exemplary methods may include determining a current light propagation data profile for the biological sample based on assay results obtained from a particle analysis system analyzing the sample. Exemplary methods may also include determining, using a computer system, a physiological status for the individual according to a calculated parameter, where the calculated parameter is based on a function of a current light propagation data measure of the current light propagation data profile, and where the physiological status provides an indication whether the individual has a normal white blood cell status. Exemplary methods may also include outputting the physiological status.

In still yet a further aspect, embodiments of the present invention encompass systems and methods for determining a treatment regimen for a patient. Exemplary methods may include accessing a current light propagation data profile concerning a biological sample of the patient, and determining, using a computer system, an estimated white blood cell status for the patient based on the current light propagation data profile. Exemplary methods may also include determining the treatment regimen for the patient based on the estimated white blood cell status. In some instances, the estimated white blood cell status includes a positive indication for a white blood cell elated disease. In some instances, the estimated white blood cell status includes a negative indication for a white blood cell related disease.

In another aspect, embodiments of the present invention encompass systems and methods for determining a treatment regimen for an individual. Exemplary methods may include accessing a current light propagation data profile concerning a biological sample of the individual, and determining, using a computer system, a physiological status for the individual according to a parameter, where the parameter is based on a current light propagation data measure of the current light propagation data profile, and where the physiological status corresponds to an estimated white blood cell status. Exemplary methods may also include determining the treatment regimen for the individual based on the physiological status for the individual.

In still another aspect, embodiments of the present invention encompass automated systems and methods for estimating a white blood cell status of an individual based on a biological sample obtained from blood of the individual. Exemplary systems include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone. An exemplary light detection assembly may include a first sensor region disposed at a first location relative to the cell interrogation zone that detects a first propagated light, a second sensor region disposed at a second location relative to the cell interrogation zone that detects a second propagated light, and a third sensor region disposed at a third location relative to the cell interrogation zone that detects an axial propagated light. In some embodiments, the system is configured to correlate a subset of DC impedance, the first propagated light, the second propagated light, and the axial light measurements from the cells of the biological sample with an estimated white blood cell status of the individual.

In yet a further aspect, embodiments of the present invention encompass systems for estimating a white blood cell status in an individual based on a biological sample obtained from blood of the individual. Exemplary systems include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. An exemplary light detection assembly may be configured to measure a first propagated light from the irradiated cells within a first range of relative to the light beam axis, a second propagated light from the irradiated cells within a second range of angles relative to the light beam axis, the second range being different than the first range, and an axial light propagated from the irradiated cells along the beam axis. In certain embodiments, the system is configured to correlate a subset of Complete Blood Cell Count platelet measurements from the cells of the biological sample combined with the subset of DC impedance, the first propagated light, the second propagated light, and the axial light measurements with the estimation of the white blood cell status in the individual. In some instances, the light detection assembly includes a first sensor zone that measures the first propagated light, a second sensor zone that measures the second propagated light, and a third sensor zone that measures the axial propagated light. In some instances, the light detection assembly includes a first sensor that measures the first propagated light, a second sensor that measures the second propagated light, and a third sensor that measures the axial propagated light. In some instances, the system is configured to correlate a subset of Complete Blood Cell Count measurements from the cells of the biological sample combined with the subset of DC impedance, the first propagated light, the second propagated light, and the axial light measurements with the estimation of the white blood cell status in the individual. In some instances, the biological sample is a blood sample of the individual.

In another aspect, embodiments of the present invention encompass systems and methods for counting a white blood cell count, for example by using a reticulocyte module in a hematological analyzer. Exemplary methods include exposing the blood sample to light in a hematological analyzer, measuring the amount of scatter at a plurality of scattering angles using the hematological analyzer, calculating the amount of scatter at predefined ones of the plurality of scattering angles using a computer, and determining, using an algorithm, executed by a computer, a population of reticulocytes separated from a population of white blood cells. Further, methods may include determining, using a computer, a count of red blood cells and white blood cells in response to the separation. In some cases, the predefined ones of the plurality of scattering angles comprise ALL, LALS, and MALS. In some cases, the step of calculating the amount of scatter at predefined ones of the plurality of scattering angles includes calculating the log of LALS. In some cases, the step of calculating the amount of scatter at predefined ones of the plurality of scattering angles includes calculating sum of the log of LALS and the log of MALS. In some cases, optical transparency of a cell or cells is measured by ALL. According to some embodiments, the step of counting the amount of WBCs includes calculating the relationship: $UWBC\#_{Retic}=RBC\#_{CBC}\times(WBC\&NRBC_{events\ Retic}/RB\text{-}C_{events\ Retic})$. According to some embodiments, the step of counting the amount of WBCs includes calculating the relationship: $UWBC\#_{Retic}=URBC\#_{CBC}\times(WBC\&NRBC_{events\ Retic}/(RBC_{events\ Retic}+WBC\&NRBC_{events\ Retic}))$. According to some embodiments, methods include correcting the WBC count by using the NRBC % from the NRBC module according the relationship: $WBC\#_{Retic}=UWBC\#_{Retic}/(1+NRBC\%_{NRBC})$. According to some embodiments, the step of counting the amount of WBCs includes calculating the relationship: $WBC\#_{Retic}=RBC\#_{CBC}\times(WBC_{events\ Retic}/RBC_{events\ Retic})$, where the WBC population does not include NRBCs.

In still a further aspect, an exemplary apparatus for counting white blood cells using a reticulocyte module may include a hematological analyzer having a light source and a detector array. The light source may be configured to irradiate the blood sample with light in the hematological analyzer. The detector array may be configured to measure the amount of light scatter at a plurality of scattering angles. Further, the apparatus may include a computer in electrical communication to the detector array. The computer may be configured to calculate the log of the amount of scatter at predefined ones of the plurality of scattering angles. In some cases, the computer may be configured to determine, using a reticulocyte module having an algorithm to identify groups, a population of the red blood cells separated from a population of white blood cells. In some cases, the computer may be configured to determine the amount of reticulocytes and white blood cells in response to the separation. According to some embodiments, the predefined ones of the plurality of scattering angles include ALL, LALS, and MALS. In some cases, the computer can be configured to calculate the log of the amount of scatter at predefined ones of the plurality of scattering angles, by calculating the log of LALS. In some cases, the computer can be configured to calculate the log of the amount of scatter at predefined ones of the plurality of scattering angles, by calculating the sum of the log of LALS and the log of MALS. In some cases, the computer can be configured to count the amount of WBCs, by calculating the relationship: $UWBC\#_{Retic}=RBC\#_{CBC}\times(WBC\&NRBC_{events\ Retic}/RB\text{-}C_{events\ Retic})$. In some cases, the computer can be configured to count an amount of WBCs in response to the amount of reticulocytes, by calculating the relationship: $UWBC\#_{Retic}=URBC\#_{CBC}\times(WBC\&NRBC_{events\ Retic}/(RB\text{-}C_{events\ Retic}+WBC\&NRBC_{events\ Retic}))$. In some cases, the computer can be configured to count an amount of WBCs, by correcting the WBC count, by using the NRBC% from the NRBC module according the relationship: $WBC\#_{Retic}=UWBC\#_{Retic}/(1+NRBC\%_{NRBC})$. In some cases, the computer can be configured to count an amount of WBCs in response to the amount of reticulocytes, by calculating the relationship: $WBC\#_{Retic}=RBC\#_{CBC}\times(WBC_{events\ Retic}/RB\text{-}C_{events\ Retic})$, where the WBC population does not include NRBCs.

Accordingly, computers, including computer components such as processing modules and the like, can be configured to calculate WBC counts using a variety of different approaches. Computers or processors may include inputs or input modules that receive parameters used to make such WBC counts, and processing modules configured to determine the WBC counts based on the input parameters. For example, computers, processors, or automated systems may include processing modules having non-transitory computer readable medium embodying machine readable code that determines the WBC count based on the functions, formulas, or equations discussed herein. Likewise, computers, processors, or automated systems may be used to implement methods where a processing module having a tangible medium embodying machine readable code determine the WBC count based on the functions, formulas, or equations discussed herein.

In another aspect, embodiments of the present invention encompass automated systems and methods for determining a white blood cell status in a biological sample. Exemplary systems include a first module, a second module, and a data processing module. The first module can be configured to determine a first red blood cell concentration of the biological sample. The second module configured to determine a combined white blood cell and nucleated red blood cell concentration of the biological sample. The second module can also be configured to determine a second red blood cell concentration of the biological sample. The data processing module can be configured to determine the white blood cell status based on a multiplication product of a first factor and a second factor, where the first factor includes the first red blood cell concentration, and the second factor includes a ratio of the combined white blood cell and nucleated red blood cell concentration to the second red blood cell concentration. In some cases, the data processing module can be configured to determine the white blood cell status, as explained elsewhere herein, according to the formula: $UWBC\#_{Retic}=RBC\#_{CBC}\times(WBC\&NRBC_{events\ Retic}/RBC_{events\ Retic})$. According to some embodiments, the biological sample is unlysed. In some cases, the first red blood cell concentration is a total red blood cell concentration. In some cases, the total red blood cell concentration includes a combined mature red blood cell and reticulocyte concentration. According to some embodiments, a system may include a third module that is configured to determine a nucleated red blood cell percentage of the biological sample. The data processing module can be configured to determine an adjusted white blood cell status based on the first red blood cell concentration, the combined white blood cell and nucleated red blood cell concentration, the second red blood cell concentration, and the nucleated red blood cell percentage. In some cases, the determination of the adjusted white blood cell status can be based on a ratio of the white blood cell status to the nucleated red blood cell percentage of the biological sample. Hence, for example, the data processing module can be configured to determine the adjusted white blood cell status, as explained elsewhere herein, according to the formula: $WBC\#_{Retic}=UWBC\#_{Retic}/(1+NRBC\%_{NRBC})$. According to some embodiments, the second module can be configured to determine an estimated white blood cell concentration of the biological sample, and the data processing module can be configured to determine an adjusted white blood cell status based on a multiplication product of the first red blood cell concentration and a ratio of the estimated white blood cell concentration to the second red blood cell concentration. Hence, for example, the data processing module can be configured to determine the adjusted white blood cell status, as explained elsewhere herein, according to the formula: $WBC\#_{Retic}=RBC\#_{CBC}\times(WBC_{events\ Retic}/RBC_{events\ Retic})$. According to some embodiments, a system may further include an optical element having a cell interrogation zone, a flow path configured to deliver a hydrodynamically focused stream of the biological sample toward the cell interrogation zone, an electrode assembly configured to measure direct current (DC) impedance of cells of the biological sample passing individually through the cell interrogation zone, a light source oriented to direct a light beam along a beam axis to irradiate the cells of the biological sample individually passing through the cell interrogation zone, and a light detection assembly optically coupled to the cell interrogation zone so as to measure light scattered by and transmitted through the irradiated cells of the biological sample. The light detection assembly can be configured to measure a first propagated light from the irradiated cells within a first range of relative to the light beam axis, a second propagated light from the irradiated cells within a second range of angles relative to the light beam axis, where the second range is different than the first range, and an axial light propagated from the irradiated cells along the beam axis. Further, a system may include an aperture bath configured to determine the first red blood cell concentration of the biological sample. The data processing module can be configured to correlate a first subset of the DC impedance, the first propagated light, the second propagated light, and the axial light measurements from the cells of the biological sample to determine the combined white blood cell and nucleated red blood cell concentration. Further, the data processing module can be configured to correlate a second subset of the DC impedance, the first propagated light, the second propagated light, and the axial light measurements from the cells of the biological sample to determine the second red blood cell concentration. In some cases, the first subset includes the first propagated light and the axial light measurements, where the first propagated light measurement includes a low angle light scatter (LALS) measurement and the axial light measurement includes an axial light loss (ALL) measurement. In some cases, the second subset includes the DC impedance and the first propagated light measurements. According to some embodiments, the determination of the white blood cell status includes a determination of white blood cell concentration. According to some embodiments, the data processing module can be configured to determine the white blood cell concentration as a count of white blood cells per volume of blood.

In still another aspect, embodiments of the present invention encompass automated methods for determining a white blood cell status in a biological sample. Exemplary methods include determining, using a first module, a first red blood cell concentration of the biological sample. Exemplary methods may also include determining, using a second module, a combined white blood cell and nucleated red blood cell concentration of the biological sample, and a second red blood cell concentration of the biological sample. Further, exemplary methods may include determining, using a data processing module, the white blood cell status based on a multiplication product of a first factor and a second factor. The first factor can include the first red blood cell concentration. The second factor can include a ratio of the combined white blood cell and nucleated red blood cell concentration to the second red blood cell concentration. In some cases, the biological sample is unlysed. In some cases, the first red blood cell concentration is a total red blood cell concentration. In some cases, the total red blood cell concentration includes a combined mature red blood cell and reticulocyte concentration. According to some embodiments, methods may further include determining, using a third module, a nucleated red blood cell percentage of the biological sample. In some cases, the step of determining the white blood cell status includes determining an adjusted white blood cell status based on the first red blood cell concentration, the combined white blood cell and nucleated red blood cell concentration, the second red blood cell concentration, and the nucleated red blood cell percentage. According to some embodiments, the adjusted white blood cell status is determined based on a ratio of the white blood cell status to the nucleated red blood cell percentage of the biological sample. In some cases, methods may further include determining, using the second module, an estimated white blood cell concentration of the biological sample, and also determining, using the data processing module, an adjusted white blood cell status based on a multiplication product of the first red blood cell concentration and a ratio of the estimated white blood cell concentration to the second red blood cell concentration. According to some embodiments, methods may also include delivering a hydrodynamically focused stream of the biological sample toward a cell interrogation zone of an optical element, measuring current (DC) impedance of cells of the biological sample passing individually through the cell interrogation zone by using an electrode assembly, and irradiating cells of the biological sample individually passing through the cell interrogation zone by using an electromagnetic beam having an axis. Methods may also include measuring a first propagated light from the irradiated cells within a first range of relative to the beam axis, using a light detection assembly. Methods may also include measuring a second propagated light from the irradiated cells within a second range of angles relative to the beam axis, where the second range is different than the first range, using the light detection assembly. Further, methods may include measuring axial light propagated from the irradiated cells along the beam axis, using the light detection assembly. In some methods, the second module determines the combined white blood cell and nucleated red blood cell concentration based on a first subset of DC impedance, the first propagated light, the second propagated light, and the axial light measurements from the cells of the biological sample. In some methods, the second module determines the second red blood cell concentration based on a second subset of DC impedance, the first propagated light, the second propagated light, and the axial light measurements from the cells of the biological sample. In some cases, the first subset includes the first propagated light and the axial light measurements. In some cases, the first propagated light measurement includes a low angle light scatter (LALS) measurement and the axial light measurement includes an axial light loss (ALL) measurement. In some cases, the second subset comprises the DC impedance and the first propagated light measurements. According to some embodiments, the step of determining the white blood cell status includes determining the white blood cell concentration. According to some embodiments, the step of determining the white blood cell status using a data processing module includes determining a white blood cell concentration as a count of white blood cells per volume of blood.

In yet another aspect, embodiments of the present invention encompass automated systems for determining a white blood cell status of a biological sample. Exemplary systems include a red blood cell bath module for obtaining a first sample data of the biological sample, where the first sample data includes a first red blood cell concentration of the biological sample. Systems may also include a transducer for obtaining a second sample data of the biological sample as the sample passes through an aperture, where the second sample data includes an axial light loss measurement, a light scatter measurement, a current measurement, or a combination thereof. Systems may also include a processor, and a storage medium having a computer application that, when executed by the processor, is configured to cause the system to determine, based on the second sample data, a combined white blood cell and nucleated red blood cell concentration of the biological sample, and also a second red blood cell concentration of the biological sample. The computer application can also, when executed by the processor, be configured to cause the system to determine the white blood cell status of the biological sample based on a multiplication product of a first factor and a second factor. The first factor can include the first red blood cell concentration. The second factor can include a ratio of the combined white blood cell and nucleated red blood cell concentration to the second red blood cell concentration. The computer application can further, when executed by the processor, be configured to cause the system to output from the processor information relating to the determined white blood cell status. Such information can include a white blood cell concentration or count, for example. According to some embodiments, the processor, the storage medium, or both, can be incorporated within a computer. In some cases, the computer can be in remote communication with a hematology machine via a network. In some cases, the computer can be in direct communication with a hematology machine. In some cases, the computer can be implemented as part of a hematology machine. According to some embodiments, the computer application, when executed by the processor, can be configured to cause the system to provide an indication that an individual may have an abnormal white blood cell status based on the determined white blood cell status of the biological sample, where the biological sample is obtained from the individual. According to some embodiments, the computer application, when executed by the processor, can be configured to cause the system to determine the white blood cell status as a white blood cell concentration. The white blood cell concentration can include a count of white blood cells per volume of blood.

In another aspect, embodiments of the present invention encompass systems and methods for determining a treatment regimen for a patient. Exemplary methods may include accessing a sample data profile concerning a biological sample of the patient, where the sample data profile includes a first red blood cell concentration of the biological sample, a combined white blood cell and nucleated red blood cell concentration of the biological sample, and a second red blood cell concentration of the biological sample. Exemplary methods may also include determining, using a computer system, a white blood cell status for the patient based on a multiplication product of a first factor and a second factor, where the first factor includes the first red blood cell concentration and the second factor includes a ratio of the combined white blood cell and nucleated red blood cell concentration to the second red blood cell concentration. Exemplary methods may further include determining the treatment regimen for the patient based on the white blood cell status. In some cases, the white blood cell status includes a positive indication for a white blood cell related disease. In some cases, the white blood cell status includes a negative indication for a white blood cell related disease. According to some embodiments, the first red blood cell concentration can be obtained using a red blood cell bath. In some cases, the combined white blood cell and nucleated red blood cell concentration of the biological sample can be determined based on a first subset of DC impedance, first propagated light, second propagated light, and axial light measurements obtained from cells of the biological sample. In some cases, the second red blood cell concentration of the biological sample can be determined based on a second subset of DC impedance, first propagated light, second propagated light, and axial light measurements obtained from cells of the biological sample. According to some embodiments, the step of determining the white blood cell status using the computer system includes determining a white blood cell concentration of the biological sample. In some cases, the white blood cell concentration includes a count of white blood cells per volume of blood.

The objects and features of the invention can be better understood with reference to the drawings described below. The drawings are not necessarily drawn to scale; emphasis is instead being placed on illustrating the principles of the disclosed subject matter. The drawings associated with the disclosure are addressed on an individual basis within the disclosure as they are introduced.

BRIEF DESCRIPTION OF THE DRAWINGS

FIG. 11 depicts aspects of a gating technique according to embodiments of the present invention.

FIG. 12 depicts aspects of a gating technique according to embodiments of the present invention.

FIG. 13 depicts aspects of a gating technique according to embodiments of the present invention.

FIG. 14 depicts aspects of a gating technique according to embodiments of the present invention.

DETAILED DESCRIPTION OF THE INVENTION

Figure 1:
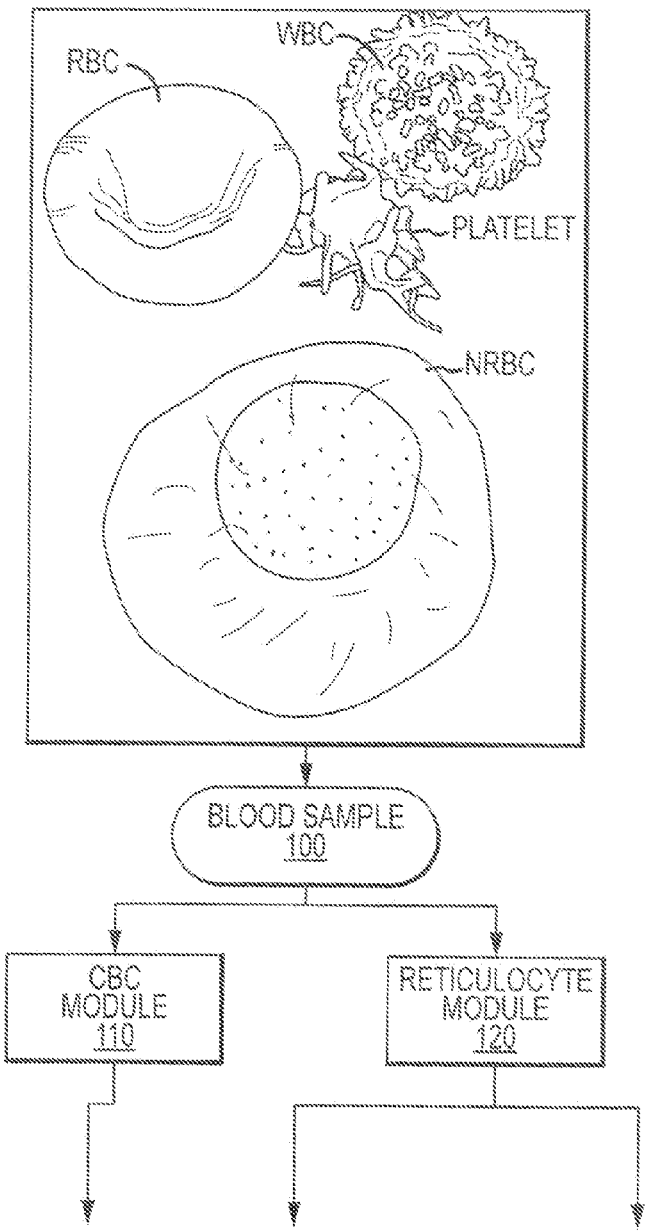
FIG. 1 illustrates aspects of blood cell analysis, according to embodiments of the present invention.

For the purposes of explanation, and in brief overview, embodiments of the present invention encompass systems and methods which involve the use a reticulocyte module in a hematological analyzer for the enumeration of white blood cell counts. An exemplary hematological cell analyzer may include a light source that produces a narrow directed beam of light toward a window in a flow cell. In various non-limiting embodiments, the light source is a laser or a laser diode, and a carrier fluid carries individual cells from a blood sample through the flow cell thereby allowing each individual cell to interact with the light beam. A plurality of photosensors located adjacent the flow cell can be used to record the intensity of light scattered at various angles by cells passing through the flow cell. In certain embodiments, one photosensor is positioned directly in the path of the light beam, and three groups of photosensors are positioned to collect light scattered by the cells in predetermined angular ranges as measured from the path of the light beam. Signals from these detectors can be transmitted to a processor, digitized, analyzed and the results displayed.

As discussed elsewhere herein, use of a reticulocyte module in a hematological analyzer can facilitate the calculation of an accurate white blood cell count. Exemplary reticulocyte modules can be configured to correctly count red blood cells where such counts usually exceed the white blood cell count by a thousand times. Exemplary reticulocyte modules can be used, with proper sample preparation, to count white cells when the WBC count is high. According to some embodiments, a standard CBC can be performed using a standard CBC module.

Typically, a hematological cell analyzer can include a light source that produces a narrow directed beam of light toward a window in a flow cell. In various non-limiting embodiments, the light source is a laser or a laser diode. A carrier fluid carries individual cells from a blood sample through the flow cell thereby allowing each individual cell to interact with the light beam.

In an exemplary embodiment, a plurality of photosensors are located adjacent the flow cell so as to record the intensity of light scattered at various angles by cells passing through the flow cell. One photosensor is positioned directly in the path of the light beam. Three groups of photosensors are positioned to collect light scattered by the cells in three predetermined angular ranges as measured from the path of the light beam. These angles are chosen to best distinguish the various blood components.

In one embodiment these predetermined angular ranges are respectively: less than 10°, which is termed Low Angle Light Scatter (LALS) and is detected by a photodetector; from about 10° to about 20° which is termed Lower Median Angle Light Scatter (LMALS) and is detected by photodetector 46; and from about 20° to about 42°, which is termed Upper Median Angle Light Scatter (UMALS) and is detected by another photodetector. The sum of the signals from the detectors for UMALS and the LMALS are collectively referred to as MALS (Median Angle Light Scatter). Signals from these detectors are transmitted to a processor, digitized, analyzed and the results displayed.

According to some embodiments, another photodetector sensor directly in the beam path measures the amount of light lost (termed axial light loss or ALL or AL2) from the light beam each time a cell passes through the beam path between the light source and the photosensor. This ALL is an indication of the transparency or absorbance of the cell or particle passing through the flow cell. The greater the light loss, the greater its absorbance.

As discussed elsewhere herein, an indicator of cell or particle size is the amount of current flowing between certain electrodes in a flow cell. As a particle enters the window region of the flow cell, current between these electrodes changes as the cell or particle blocks the current from flowing. The decrease in the amount of current flowing is related to the cell or particle size. The direct current (DC) current is supplied by a DC source. The DC module measures the change in current flow caused by ions in the fluid and is a measure of the size of the cell.

According to some embodiments, a reticulocyte module can be used to analyze blood cells of a biological sample obtained from an individual. In certain embodiments, cells of a blood sample are incubated with a reagent to stain certain cells or cell features. In one embodiment the stain New Methylene Blue (NMB) is used.

Hence, described herein are hematology systems and methods configured to assess WBC status conditions of an individual, based on a biological sample obtained from the individual. FIG. 1 illustrates aspects of an exemplary WBC count technique. As shown here, and as discussed elsewhere herein, a whole blood sample 100 may include cells such as platelets, white blood cells (WBCs), and red blood cell (RBCs), including nucleated red blood cells (NRBCs). Various RBC, WBC, and NRBC parameters, obtained from channel processing mechanisms such as a CBC module 110 or a reticulocyte module 120, can be evaluated to assess the WBC status of an individual. For example, exemplary evaluation techniques may involve obtaining a count 130 of white blood cells, based on input parameters 140 obtained from the channel processing modules 110, 120. The hematology systems and methods discussed herein can assess whether an individual is presenting with normal or abnormal WBC parameters based on data related to certain impedance, conductivity, and angular light propagation measurements of a biological sample of the individual.

Often, systems and methods will provide blood cell data in terms of a count or a concentration. In some cases, the terms count and concentration may be used interchangeably. For example, the term white blood cell count may refer to the absolute number of white blood cells or the number of white blood cells detected from a flow cytometer in a sample or aliquot, divided by the volume of the sample or aliquot. The term white blood cell concentration may refer to the white blood cell count or an estimated number associated with the white blood cell count. An exemplary white blood cell count or concentration can be between $3.5\text{-}11 \times 10^9/L$ (e.g. cells per liter of blood).

Cellular analysis systems that detect light scatter at multiple angles can be used to analyze a biological sample (e.g. a blood sample) and output a predicted WBC status of an individual. Exemplary systems are equipped with sensor assemblies that obtain light scatter data for three or more angular ranges, in addition to light transmission data associated with an extinction or axial light loss measure, and thus provide accurate, sensitive, and high resolution results without requiring the use of certain dye, antibody, or fluorescence techniques. In one instance, a hematology analyzer such as a DxH 800 Hematology Analyzer (Beckman Coulter, Brea, Calif., USA) is configured to analyze a biological sample (e.g. a blood sample) based on multiple light scatter angles and output a predicted WBC status of an individual. The DxH 800 includes various channel processing modules that are configured to recognize the morphologic features indicative of cellular components within the blood. For example, the DxH includes a reticulocyte channel processing module that is configured to analyze certain blood cell components. The DxH 800 is configured to generate a significant amount of data based on analysis of the sample, this such data, which is described in detail herein, can be referred to as CBC data or VCS data.

In some embodiments, VCS data is based on the determination of different parameters for each cell of the sample analyzed, such parameters correlating to each cell's morphology. Specifically, a volume parameter corresponding to the cell size can be measured directly by impedance. Further, a conductivity parameter corresponding to the internal cellular density can be measured directly by the conduction of radio frequency waves across the cell. What is more, five different angles (or ranges of angles) of light scatter corresponding to cytoplasmic granularity and nuclear complexity, for example, can be measured with various light detection mechanisms.

Figure 2:
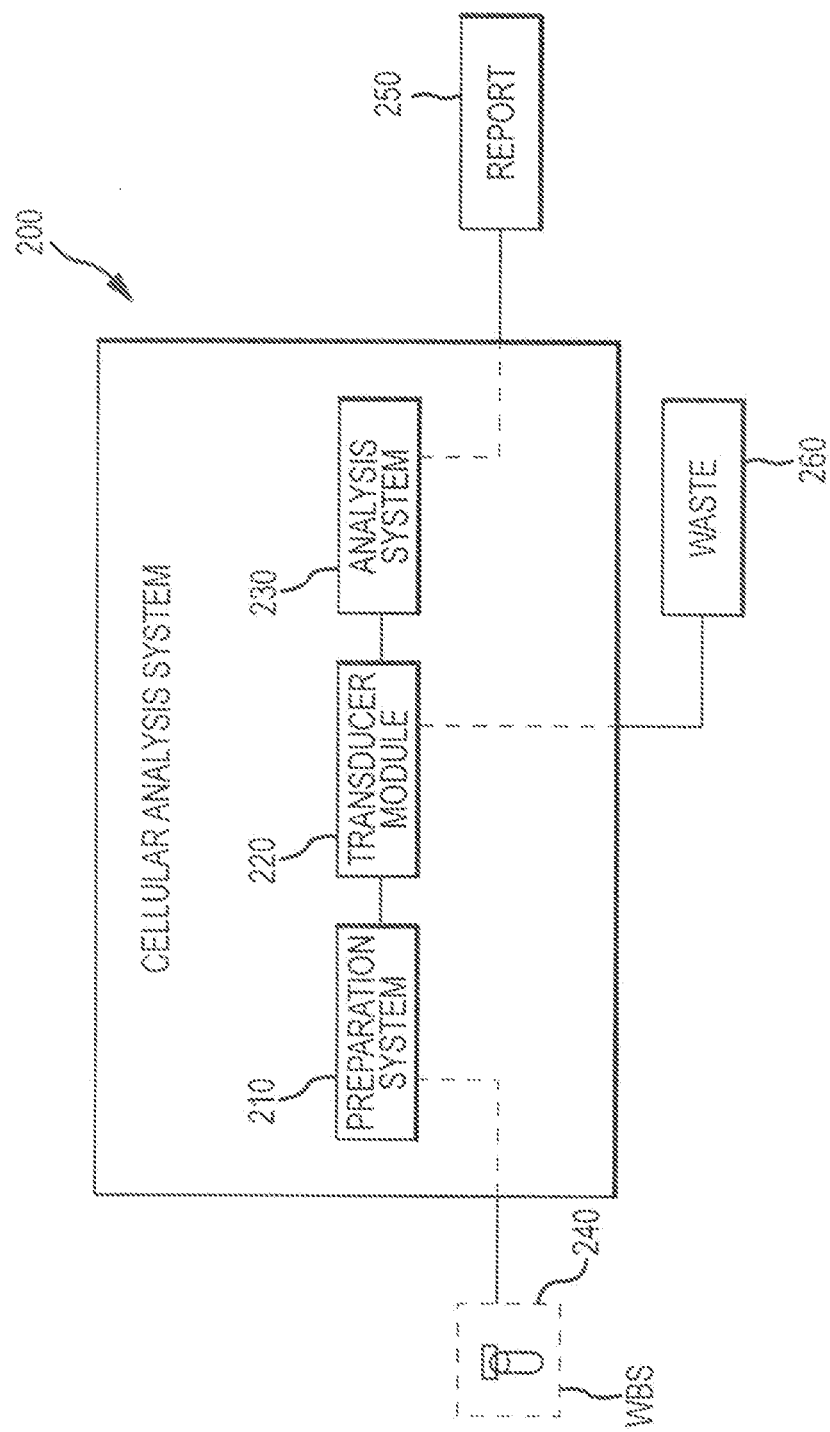
FIG. 2 schematically depicts aspects of a cellular analysis system, according to embodiments of the present invention.

FIG. 2 schematically depicts a cellular analysis system 200. As shown here, system 200 includes a preparation system 210, a transducer module 220, and an analysis system 230.

While system 200 is herein described at a very high level, with reference to the three core system blocks (210, 220, and 230), the skilled artisan would readily understand that system 200 includes many other system components such as central control processor(s), display system(s), fluidic system(s), temperature control system(s), user-safety control system(s), and the like. In operation, a whole blood sample (WBS) 240 can be presented to the system 200 for analysis. In some instances, WBS 240 is aspirated into system 200. Exemplary aspiration techniques are known to the skilled artisan. After aspiration, WBS 240 can be delivered to a preparation system 210. Preparation system 210 receives WBS 240 and can perform operations involved with preparing WBS 240 for further measurement and analysis. For example, preparation system 210 may separate WBS 240 into predefined aliquots for presentation to transducer module 220. Preparation system 210 may also include mixing chambers so that appropriate reagents may be added to the aliquots. For example, where an aliquot is to be tested for differentiation of white blood cell subset populations, a lysing reagent (e.g. ERYTHROLYSE, a red blood cell lysing buffer) may be added to the aliquot to break up and remove the RBCs. Preparation system 210 may also include temperature control components to control the temperature of the reagents and/or mixing chambers. Appropriate temperature controls can improve the consistency of the operations of preparation system 210. As discussed elsewhere herein, sample data such as light scatter data, light absorption data, and/or current data can be obtained (e.g. using a transducer) and processed or used to determine various blood cell status indications of an individual patient.

In some instances, predefined aliquots can be transferred from preparation system 210 to transducer module 220. As described in further detail below, transducer module 220 can perform direct current (DC) impedance, radiofrequency (RF) conductivity, light transmission, and/or light scatter measurements of cells from the WBS passing individually therethrough. Measured DC impedance, RF conductivity, and light propagation (e.g. light transmission, light scatter) parameters can be provided or transmitted to analysis system 230 for data processing. In some instances, analysis system 230 may include computer processing features and/or one or more modules or components such as those described herein with reference to the system depicted in FIG. 6 and described further below, which can evaluate the measured parameters, identify and enumerate the blood cellular constituents, and correlate a subset of data characterizing elements of the WBS with a WBC status of the individual. As shown here, cellular analysis system 200 may generate or output a report 250 containing the predicted WBC status and/or a prescribed treatment regimen for the individual. In some instances, excess biological sample from transducer module 220 can be directed to an external (or alternatively internal) waste system 260.

Treatment regimens may involve administration of one or more medications or therapeutic agents to an individual for the purposes of addressing the patient's condition. Any of a variety of therapeutic modalities can be used for treating an individual identified as having an abnormal WBC count or condition as discussed herein.

Figure 3:
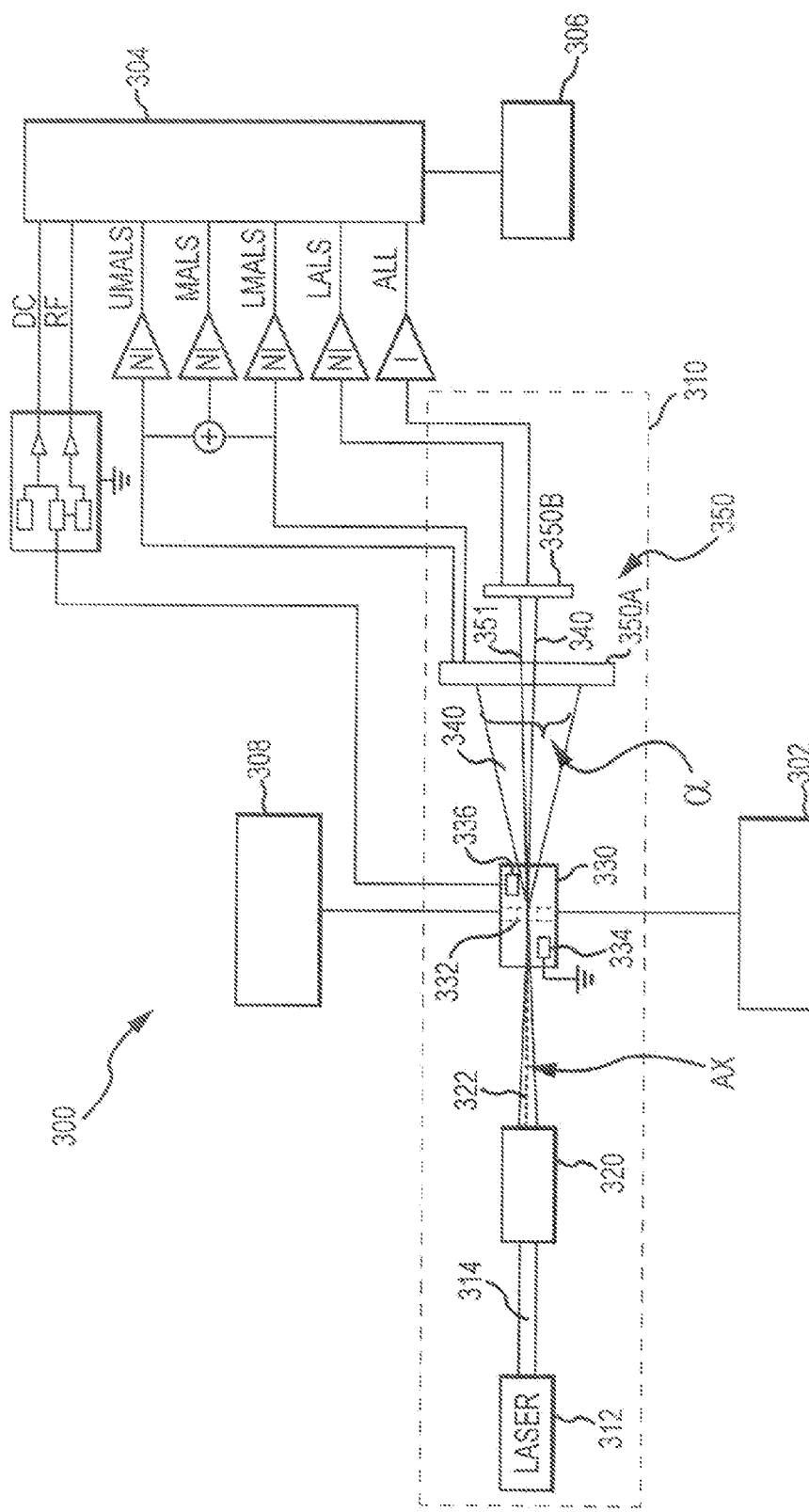
FIG. 3 provides a system block diagram illustrating aspects of a cellular analysis system according to embodiments of the present invention.

FIG. 3 illustrates in more detail a transducer module and associated components in more detail. As shown here, system 300 includes a transducer module 310 having a light or irradiation source such as a laser 310 emitting a beam 314. The laser 312 can be, for example, a 635 nm, 5 mW, solid-state laser. In some instances, system 300 may include a focus-alignment system 320 that adjusts beam 314 such that a resulting beam 322 is focused and positioned at a cell interrogation zone 332 of a flow cell 330. In some instances, flow cell 330 receives a sample aliquot from a preparation system 302. As described elsewhere herein, various fluidic mechanisms and techniques can be employed for hydrodynamic focusing of the sample aliquot within flow cell 330.

In some instances, the aliquot generally flows through the cell interrogation zone 332 such that its constituents pass through the cell interrogation zone 332 one at a time. In some cases, a system 300 may include a cell interrogation zone or other feature of a transducer module or blood analysis instrument such as those described in U.S. Pat. Nos. 5,125,737; 6,228,652; 7,390,662; 8,094,299; and 8,189,187, the contents of which are incorporated herein by references. For example, a cell interrogation zone 332 may be defined by a square transverse cross-section measuring approximately 50×50 microns, and having a length (measured in the direction of flow) of approximately 65 microns. Flow cell 330 may include an electrode assembly having first and second electrodes 334, 336 for performing DC impedance and RF conductivity measurements of the cells passing through cell interrogation zone 332. Signals from electrodes 334, 336 can be transmitted to analysis system 304. The electrode assembly can analyze volume and conductivity characteristics of the cells using low-frequency current and high-frequency current, respectively. For example, low-frequency DC impedance measurements can be used to analyze the volume of each individual cell passing through the cell interrogation zone. Relatedly, high-frequency RF current measurements can be used to determine the conductivity of cells passing through the cell interrogation zone. Because cell walls act as conductors to high frequency current, the high frequency current can be used to detect differences in the insulating properties of the cell components, as the current passes through the cell walls and through each cell interior. High frequency current can be used to characterize nuclear and granular constituents and the chemical composition of the cell interior.

Incoming beam 322 travels along beam axis AX and irradiates the cells passing through cell interrogation zone 332, resulting in light propagation within an angular range a (e.g. scatter, transmission) emanating from the zone 332. Exemplary systems are equipped with sensor assemblies that can detect light within three, four, five, or more angular ranges within the angular range a, including light associated with an extinction or axial light loss measure as described elsewhere herein. As shown here, light propagation 340 can be detected by a light detection assembly 350, optionally having a light scatter detector unit 350A and a light scatter and transmission detector unit 350B. In some instances, light scatter detector unit 350A includes a photoactive region or sensor zone for detecting and measuring upper median angle light scatter (UMALS), for example light that is scattered or otherwise propagated at angles relative to a light beam axis within a range from about 20 to about 42 degrees. In some instances, UMALS corresponds to light propagated within an angular range from between about 20 to about 43 degrees, relative to the incoming beam axis which irradiates cells flowing through the interrogation zone. Light scatter detector unit 350A may also include a photoactive region or sensor zone for detecting and measuring lower median angle light scatter (LMALS), for example light that is scattered or otherwise propagated at angles relative to a light beam axis within a range from about 10 to about 20 degrees. In some instances, LMALS corresponds to light propagated within an angular range from between about 9 to about 19 degrees, relative to the incoming beam axis which irradiates cells flowing through the interrogation zone.

A combination of UMALS and LMALS is defined as median angle light scatter (MALS), which is light scatter or propagation at angles between about 9 degrees and about 43 degrees relative to the incoming beam axis which irradiates cells flowing through the interrogation zone.

As shown in FIG. 3, the light scatter detector unit 350A may include an opening 351 that allows low angle light scatter or propagation 340 to pass beyond light scatter detector unit 350A and thereby reach and be detected by light scatter and transmission detector unit 350B. According to some embodiments, light scatter and transmission detector unit 350B may include a photoactive region or sensor zone for detecting and measuring lower angle light scatter (LALS), for example light that is scattered or propagated at angles relative to an irradiating light beam axis of about 5.1 degrees. In some instances, LALS corresponds to light propagated at an angle of less than about 9 degrees, relative to the incoming beam axis which irradiates cells flowing through the interrogation zone. In some instances, LALS corresponds to light propagated at an angle of less than about 10 degrees, relative to the incoming beam axis which irradiates cells flowing through the interrogation zone. In some instances, LALS corresponds to light propagated at an angle of about 1.9 degrees±0.5 degrees, relative to the incoming beam axis which irradiates cells flowing through the interrogation zone. In some instances, LALS corresponds to light propagated at an angle of about 3.0 degrees±0.5 degrees, relative to the incoming beam axis which irradiates cells flowing through the interrogation zone. In some instances, LALS corresponds to light propagated at an angle of about 3.7 degrees±0.5 degrees, relative to the incoming beam axis which irradiates cells flowing through the interrogation zone. In some instances, LALS corresponds to light propagated at an angle of about 5.1 degrees±0.5 degrees, relative to the incoming beam axis which irradiates cells flowing through the interrogation zone. In some instances, LALS corresponds to light propagated at an angle of about 7.0 degrees±0.5 degrees, relative to the incoming beam axis which irradiates cells flowing through the interrogation zone.

According to some embodiments, light scatter and transmission detector unit 350B may include a photoactive region or sensor zone for detecting and measuring light transmitted axially through the cells, or propagated from the irradiated cells, at an angle of 0 degrees relative to the incoming light beam axis. In some cases, the photoactive region or sensor zone may detect and measure light propagated axially from cells at angles of less than about 1 degree relative to the incoming light beam axis. In some cases, the photoactive region or sensor zone may detect and measure light propagated axially from cells at angles of less than about 0.5 degrees relative to the incoming light beam axis less. Such axially transmitted or propagated light measurements correspond to axial light loss (ALL or AL2). As noted in previously incorporated U.S. Pat. No. 7,390,662, when light interacts with a particle, some of the incident light changes direction through the scattering process (i.e. light scatter) and part of the light is absorbed by the particles. Both of these processes remove energy from the incident beam. When viewed along the incident axis of the beam, the light loss can be referred to as forward extinction or axial light loss. Additional aspects of axial light loss measurement techniques are described in U.S. Pat. No. 7,390,662 at column 5, line 58 to column 6, line 4.

As such, the cellular analysis system 300 provides means for obtaining light propagation measurements, including light scatter and/or light transmission, for light emanating from the irradiated cells of the biological sample at any of a variety of angles or within any of a variety of angular ranges, including ALL and multiple distinct light scatter or propagation angles. For example, light detection assembly 350, including appropriate circuitry and/or processing units, provides a means for detecting and measuring UMALS, LMALS, LALS, MALS, and ALL.

Wires or other transmission or connectivity mechanisms can transmit signals from the electrode assembly (e.g. electrodes 334, 336), light scatter detector unit 350A, and/or light scatter and transmission detector unit 350B to analysis system 304 for processing. For example, measured DC impedance, RF conductivity, light transmission, and/or light scatter parameters can be provided or transmitted to analysis system 304 for data processing. In some instances, analysis system 304 may include computer processing features and/or one or more modules or components such as those described herein with reference to the system depicted in FIG. 6, which can evaluate the measured parameters, identify and enumerate biological sample constituents, and correlate a subset of data characterizing elements of the biological sample with a WBC status of the individual. As shown here, cellular analysis system 300 may generate or output a report 306 containing the predicted WBC status and/or a prescribed treatment regimen for the individual. In some instances, excess biological sample from transducer module 310 can be directed to an external (or alternatively internal) waste system 308. In some instances, a cellular analysis system 300 may include one or more features of a transducer module or blood analysis instrument such as those described in previously incorporated U.S. Pat. Nos. 5,125,737; 6,228,652; 8,094,299; and 8,189,187.

Figure 4:
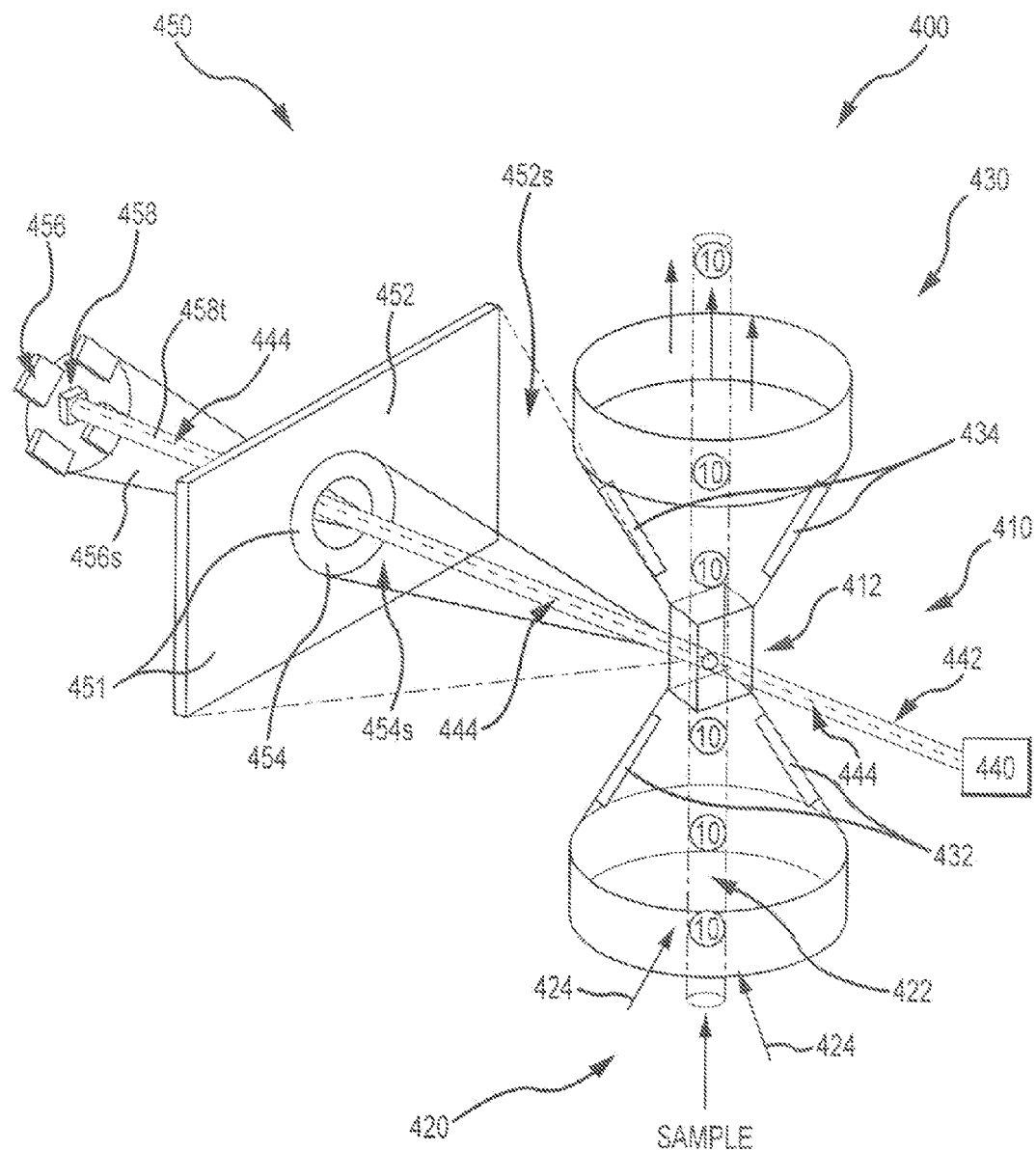
FIG. 4 illustrates aspects of an automated cellular analysis system for evaluating the white blood cell status of an individual, according to embodiments of the present invention.

FIG. 4 illustrates aspects of an automated cellular analysis system for predicting or assessing a WBC status of an individual, according to embodiments of the present invention. In particular, the WBC status can be predicted based on a biological sample obtained from blood of the individual. As shown here, an analysis system or transducer 400 may include an optical element 410 having a cell interrogation zone 412. The transducer also provides a flow path 420, which delivers a hydrodynamically focused stream 422 of a biological sample toward the cell interrogation zone 412. For example, as the sample stream 422 is projected toward the cell interrogation zone 412, a volume of sheath fluid 424 can also enter the optical element 410 under pressure, so as to uniformly surround the sample stream 422 and cause the sample stream 422 to flow through the center of the cell interrogation zone 412, thus achieving hydrodynamic focusing of the sample stream. In this way, individual cells of the biological sample, passing through the cell interrogation zone one cell at a time, can be precisely analyzed.

Transducer module or system 400 also includes an electrode assembly 430 that measures direct current (DC) impedance and radiofrequency (RF) conductivity of cells 10 of the biological sample passing individually through the cell interrogation zone 412. The electrode assembly 430 may include a first electrode mechanism 432 and a second electrode mechanism 434. As discussed elsewhere herein, low-frequency DC measurements can be used to analyze the volume of each individual cell passing through the cell interrogation zone. Relatedly, high-frequency RF current measurements can be used to determine the conductivity of cells passing through the cell interrogation zone. Such conductivity measurements can provide information regarding the internal cellular content of the cells. For example, high frequency RF current can be used to analyze nuclear and granular constituents, as well as the chemical composition of the cell interior, of individual cells passing through the cell interrogation zone.

The system 400 also includes a light source 440 oriented to direct a light beam 442 along a beam axis 444 to irradiate the cells 10 of the biological sample individually passing through the cell interrogation zone 412. Relatedly, the system 400 includes a light detection assembly 450 optically coupled with the cell interrogation zone, so as to measure light scattered by and transmitted through the irradiated cells 10 of the biological sample. The light detection assembly 450 can include a plurality of light sensor zones that detect and measure light propagating from the cell interrogation zone 412. In some instances, the light detection assembly detects light propagated from the cell interrogation zone at various angles or angular ranges relative to the irradiating beam axis. For example, light detection assembly 450 can detect and measure light that is scattered at various angles by the cells, as well as light that is transmitted axially by the cells along the beam axis. The light detection assembly 450 can include a first sensor zone 452 that measures a first scattered or propagated light 452s within a first range of angles relative to the light beam axis 444. The light detection assembly 450 can also include a second sensor zone 454 that measures a second scattered or propagated light 454s within a second range of angles relative to the light beam axis 444. As shown here, the second range of angles for scattered or propagated light 454s is different from the first range of angles for scattered or propagated light 452s. Further, the light detection assembly 450 can include a third sensor zone 456 that measures a third scattered or propagated light 456s within a third range of angles relative to the light beam axis 444. As shown here, the third range of angles for scattered or propagated light 456s is different from both the first range of angles for scattered or propagated light 452s and the second range of angles for scattered or propagated light 454s. The light detection assembly 450 also includes a fourth sensor zone 458 that measures axial light 458t transmitted through the cells of the biological sample passing individually through the cell interrogation zone 412 or propagated from the cell interrogation zone along the axis beam. In some instances, each of the sensor zones 452, 454, 456, and 458 are disposed at a separate sensor associated with that specific sensor zone. In some instances, one or more of the sensor zones 452, 454, 456, and 458 are disposed on a common sensor of the light detection assembly 450. For example, the light detection assembly may include a first sensor 451 that includes first sensor zone 452 and second sensor zone 454. Hence, a single sensor may be used for detecting or measuring two or more types (e.g. low angle, medium angle, or high angle) of light scatter or propagation.

Figure 4A:
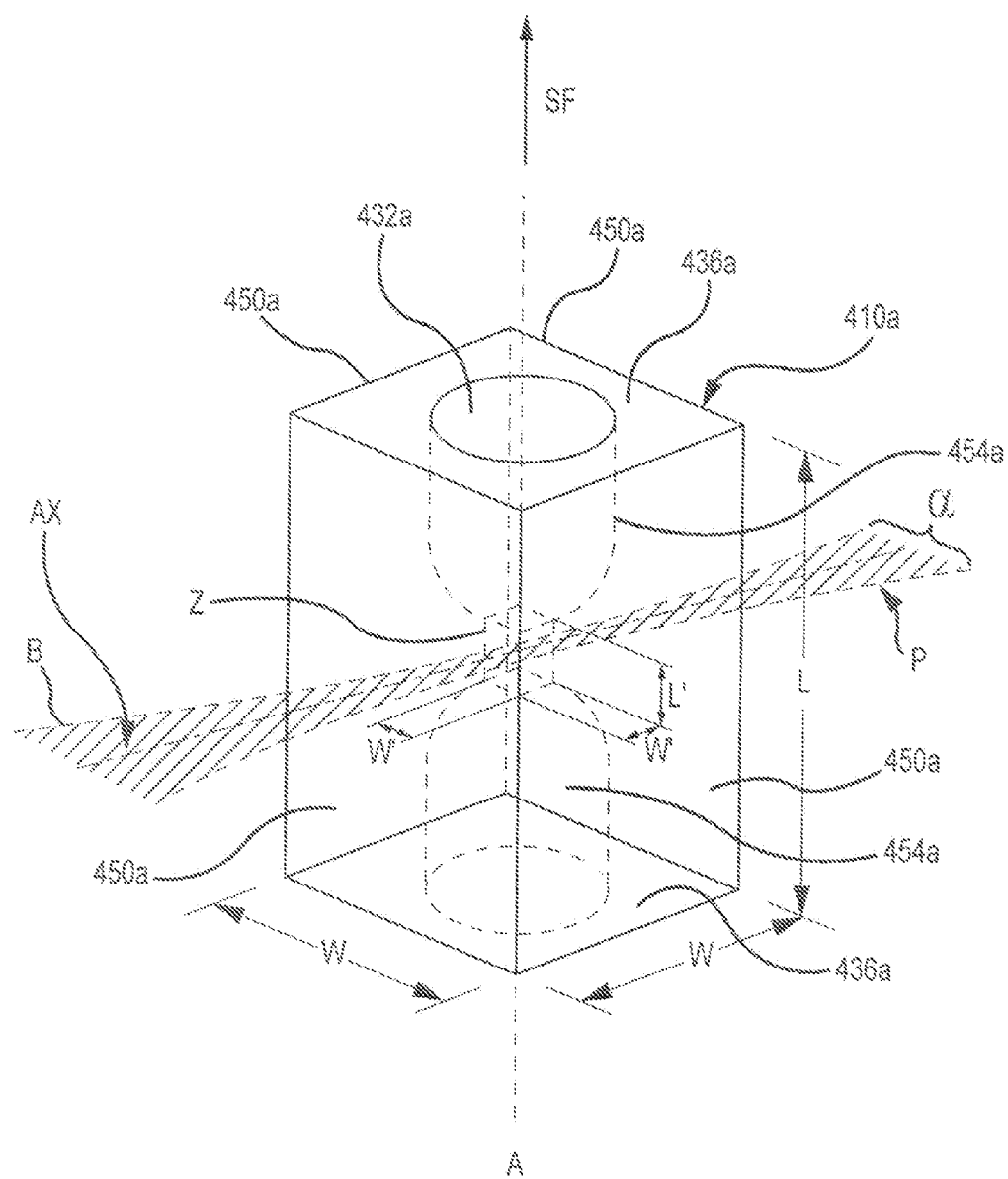
FIG. 4A shows aspects of an optical element of a cellular analysis system, according to embodiments of the present invention.

Automated cellular analysis systems may include any of a variety of optical elements or transducer features. For example, as depicted in FIG. 4A, an optical element 410a of a cellular analysis system transducer may have a square prism shape, with four rectangular, optically flat sides 450a and opposing end walls 436a. In some instances, the respective widths W of each side 450a are the same, each measuring about 4.2 mm, for example. In some instances, the respective lengths L of each side 450a are the same, each measuring about 6.3 mm, for example. In some instances, all or part of the optical element 410a may be fabricated from fused silica, or quartz. A flow passageway 432a formed through a central region of optical element 410a may be concentrically configured with respect to a longitudinal axis A passing through the center of element 410a and parallel to a direction of sample-flow as indicated by arrow SF. Flow passageway 432a includes a cell interrogation zone Z and a pair of opposing tapered bore holes 454a having openings in the vicinity of their respective bases that fluidically communicate with the cell interrogation zone. In some instances, the transverse cross-section of the cell interrogation zone Z is square in shape, the width W' of each side nominally measuring 50 microns±10 microns. In some instances, the length L' of the cell interrogation zone Z, measured along axis A, is about 1.2 to 1.4 times the width W' of the interrogation zone. For example, the length L' may be about 65 microns±10 microns. As noted elsewhere herein, DC and RF measurements can be made on cells passing through the cell interrogation zone. In some instances, the maximum diameter of the tapered bore holes 454a, measured at end walls 436a, is about 1.2 mm. An optical structure 410a of the type described can be made from a quartz square rod containing a 50×50 micron capillary opening, machined to define the communicating bore holes 454a, for example. A laser or other irradiation source can produce a beam B that is directed through or focused into the cell interrogation zone. For example, the beam may be focused into an elliptically shaped waist located within the interrogation zone Z at a location through which the cells are caused to pass. A cellular analysis system may include a light detection assembly that is configured to detect light which emanates from the optical element 410a, for example light P that is propagated from the cell interrogation zone Z which contains illuminated or irradiated cells flowing therewithin. As depicted here, light P can propagate or emanate from the cell interrogation zone Z within an angular range $\alpha$, and thus can be measured or detected at selected angular positions or angular ranges relative to the beam axis AX. Relatedly, a light detection assembly can detect light scattered or axially transmitted in a forward plane within various angular ranges with respect to an axis AX of beam B. As discussed elsewhere herein, one or more light propagation measurements can be obtained for individual cells passing through the cell interrogation zone one at a time. In some cases, a cellular analysis system may include one or more features of a transducer or cell interrogation zone such as those described in U.S. Pat. Nos. 5,125,737; 6,228,652; 8,094,299; and 8,189,187, the contents of which are incorporated herein by reference.

Figure 5:
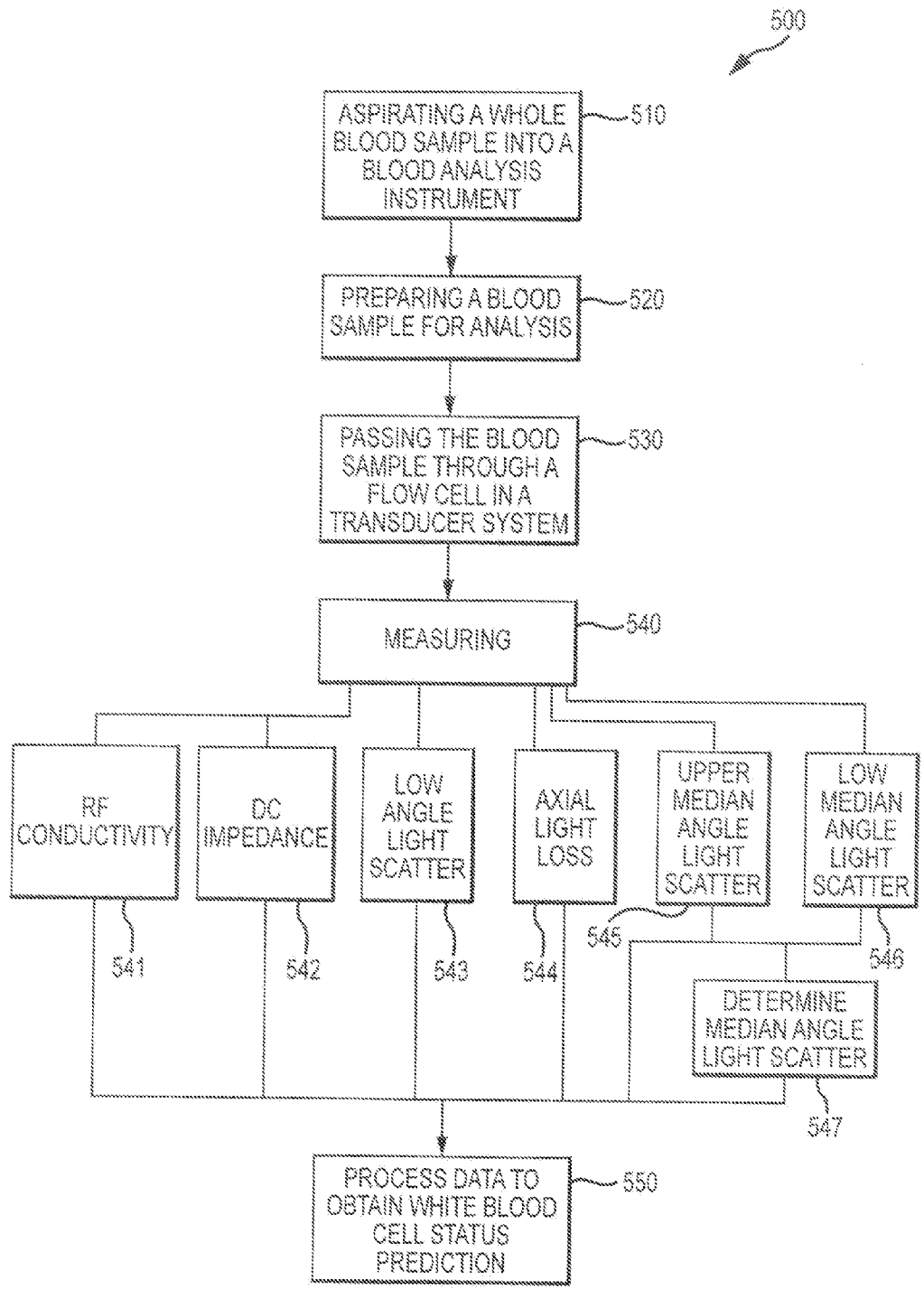
FIG. 5 depicts aspects of an exemplary method for evaluating the white blood cell status of an individual, according to embodiments of the present invention.

FIG. 5 depicts aspects of an exemplary method 500 for predicting or assessing a WBC status of an individual. Method 500 includes introducing a blood sample into a blood analysis system, as indicated by step 510. As shown in step 520, the method may also include preparing the blood sample by dividing the sample into aliquots and mixing the aliquot samples with appropriate reagents. In step 530, the samples can be passed through a flow cell in a transducer system such that sample constituents (e.g. blood cells) pass through a cell interrogation zone in a one by one fashion. The constituents can be irradiated by a light source, such as a laser. In step 540, any combination RF conductivity 541, DC impedance 542, first angular light propagation 543 (e.g. LALS), second angular light propagation 544 (e.g. AL2), third angular light propagation 545 (e.g. UMAL), and/or fourth angular light propagation 546 (e.g. LMALS) may be measured. As depicted by step 547, the third and fourth angular light propagation measurements can be used to determine a fifth angular light propagation measurement (e.g. MALS). Alternatively, MALS can be measured directly. As discussed elsewhere herein, certain measurements or combinations of measurements can be processed, as indicated by step 550, so as to provide a WBC status prediction. Optionally, methods may also include determining a treatment regime based on the predicted WBC status.

A cellular analysis system may be configured to correlate a subset of DC impedance, RF conductivity, angular light measurements (e.g. first scattered light, second scattered light) and the axial light measurements from the cells of the biological sample with a WBC status of an individual. As discussed elsewhere herein, in some instances at least a portion of the correlation can be performed using one or more software modules executable by one or more processors, one or more hardware modules, or any combination thereof. Processors or other computer or module systems may be configured to receive as an input values for the various measurements or parameters and automatically output the predicted WBC status of the individual. In some instances, one or more of the software modules, processors, and/or hardware modules may be included as a component of a hematology system that is equipped to obtain multiple light angle detection parameters, such as Beckman Coulter's UniCel® DxH™ 800 Cellular Analysis System. In some instances, one or more of the software modules, processors, and/or hardware modules may be included as a component of a stand-alone computer that is in operative communication or connectivity with a hematology system that is equipped to obtain multiple light angle detection parameters, such as Beckman Coulter's UniCel® DxH 800 System. In some instances, at least a portion of the correlation can be performed by one or more of the software modules, processors, and/or hardware modules that receive data from a hematology system that is equipped to obtain multiple light angle detection parameters, such as Beckman Coulter's UniCel® DxH 800 System remotely via the internet or any other over wired and/or wireless communication network. Relatedly, each of the devices or modules according to embodiments of the present invention can include one or more software modules on a computer readable medium that is processed by a processor, or hardware modules, or any combination thereof.

Figure 6:
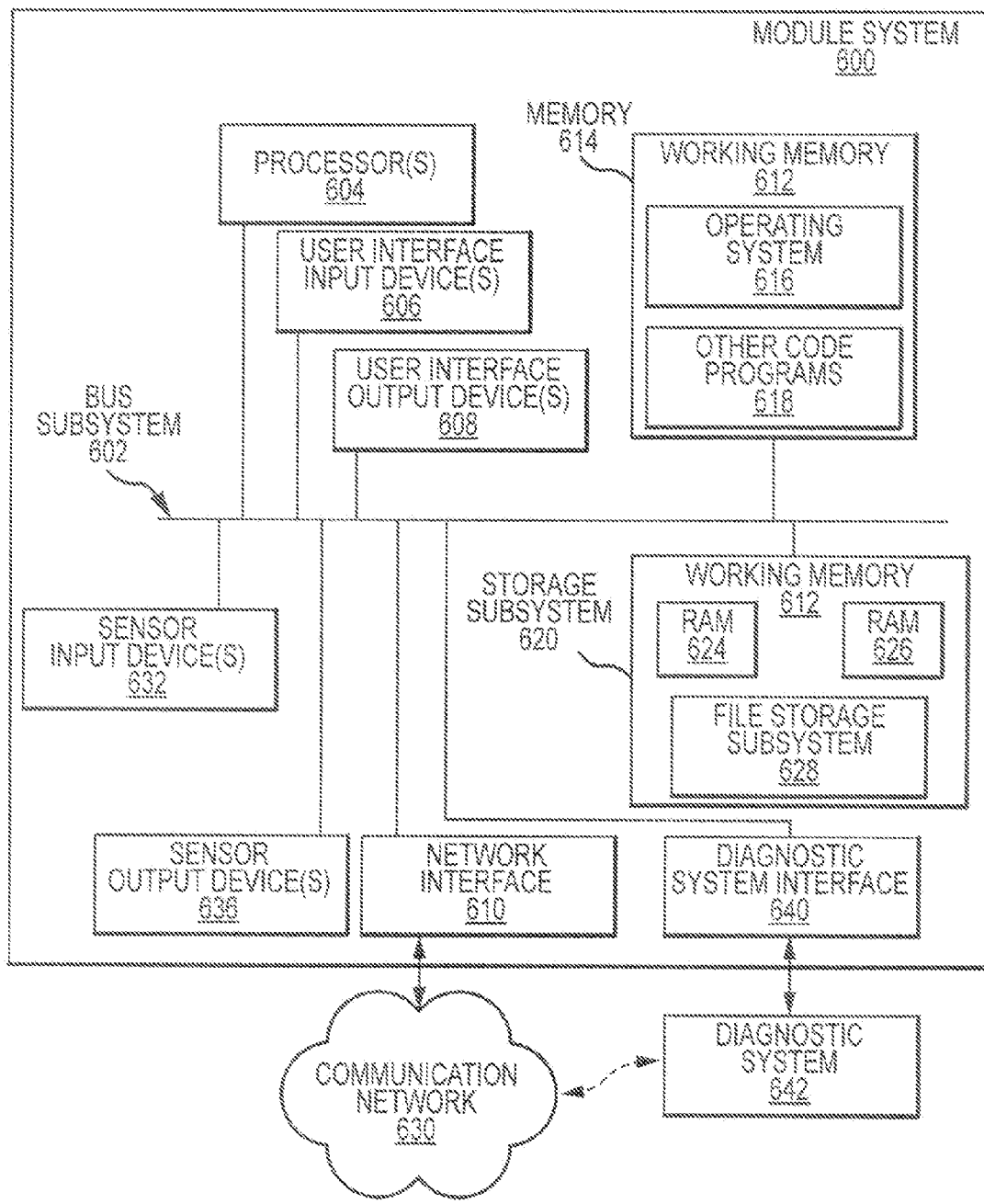
FIG. 6 provides a simplified block diagram of an exemplary module system, according to embodiments of the present invention.

FIG. 6 is a simplified block diagram of an exemplary module system that broadly illustrates how individual system elements for a module system 600 may be implemented in a separated or more integrated manner. Module system 600 may be part of or in connectivity with a cellular analysis system for predicting a WBC status of an individual according to embodiments of the present invention. Module system 600 is well suited for producing data or receiving input related to a WBC analysis. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600. In some instances, systems may include a computer-readable storage medium or other tangible storage medium that stores one or more sequences of instructions or code which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet connection communications.

It is appreciated that system 600 can be configured to carry out various aspects of methods of the present invention. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain multiple light angle detection parameters, such as Beckman Coulter's UniCel® DxH™ 800 Cellular Analysis System. In some instances, user interface input device(s) 606 and/or network interface 610 may be configured to receive cellular parameter signals generated by a cellular analysis system that is equipped to obtain multiple light angle detection parameters, such as Beckman Coulter's UniCel® DxH™ 800 Cellular Analysis System. In some instances, diagnostic system 642 may include or be part of a cellular analysis system that is equipped to obtain multiple light angle detection parameters, such as Beckman Coulter's UniCel® DxH™ 800 Cellular Analysis System.

Processor component or module 604 can also be configured to transmit cellular parameter signals, optionally processed according to any of the techniques disclosed herein, to sensor output device or module 636, to user interface output device or module 608, to network interface device or module 610, to diagnostic system interface 640, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600 to a user.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other parties. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain multiple light angle detection parameters, such as such as Beckman Coulter's UniCel® DxH™ 800 Cellular Analysis System.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 6 is intended only as a specific example for purposes of illustrating one or more embodiments of the present invention. Many other configurations of module system 600 are possible having more or less components than the module system depicted in FIG. 6. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where a WBC status is predicted or determined. The predicted WBC status can be output to a system user via an output module. In some cases, the module system 600 can determine an initial treatment or induction protocol for the patient, or an adjusted treatment protocol, based on one or more cellular analysis parameters and/or the predicted WBC status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Relatedly, in some instances a system includes a processor configured to receive VCS data as input. A processor may also be configured to receive CBC data as input. Optionally, a processor, storage medium, or both, may be incorporated within a hematology or cellular analysis machine. In some instances, the hematology machine may generate VCS data, CBC data, or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Volume Conductivity Scatter (VCS) Data

In addition to CBC data, which may be obtained from a CBC module, VCS data may be obtained from a VCS module. Exemplary VCS parameters include the following:
1. Cell Conductivity (C) [high frequency current]
2. Cell Volume (V) [low frequency current]
3. Axial light loss or absorbed light (AL2 or ALL)
4. Low-angle light scatter (LALS)
5. Upper median-angle light scatter (UMALS)
6. Lower median-angle light scatter (LMALS)
7. Median-angle light scatter (MALS) [UMALS+LMALS]

In this way, various parameters (e.g. volume, conductivity, and angles of light scatter or propagation) can be calculated separately for blood cells such as white blood cells, red blood cells, and platelets. This data can be obtained based on a biological sample of an individual. What is more, CBC and VCS data can be viewed on the screen of an instrument, for example as shown in the screen shot 700 depicted in FIG. 7, as well as automatically exported as an Excel file. Hence, blood cells (e.g. RBC's, platelets, and WBC's) can be analyzed and individually plotted in tri-dimensional histograms, with the position of each cell on the histogram being defined by certain parameters as described herein.

Figure 7:
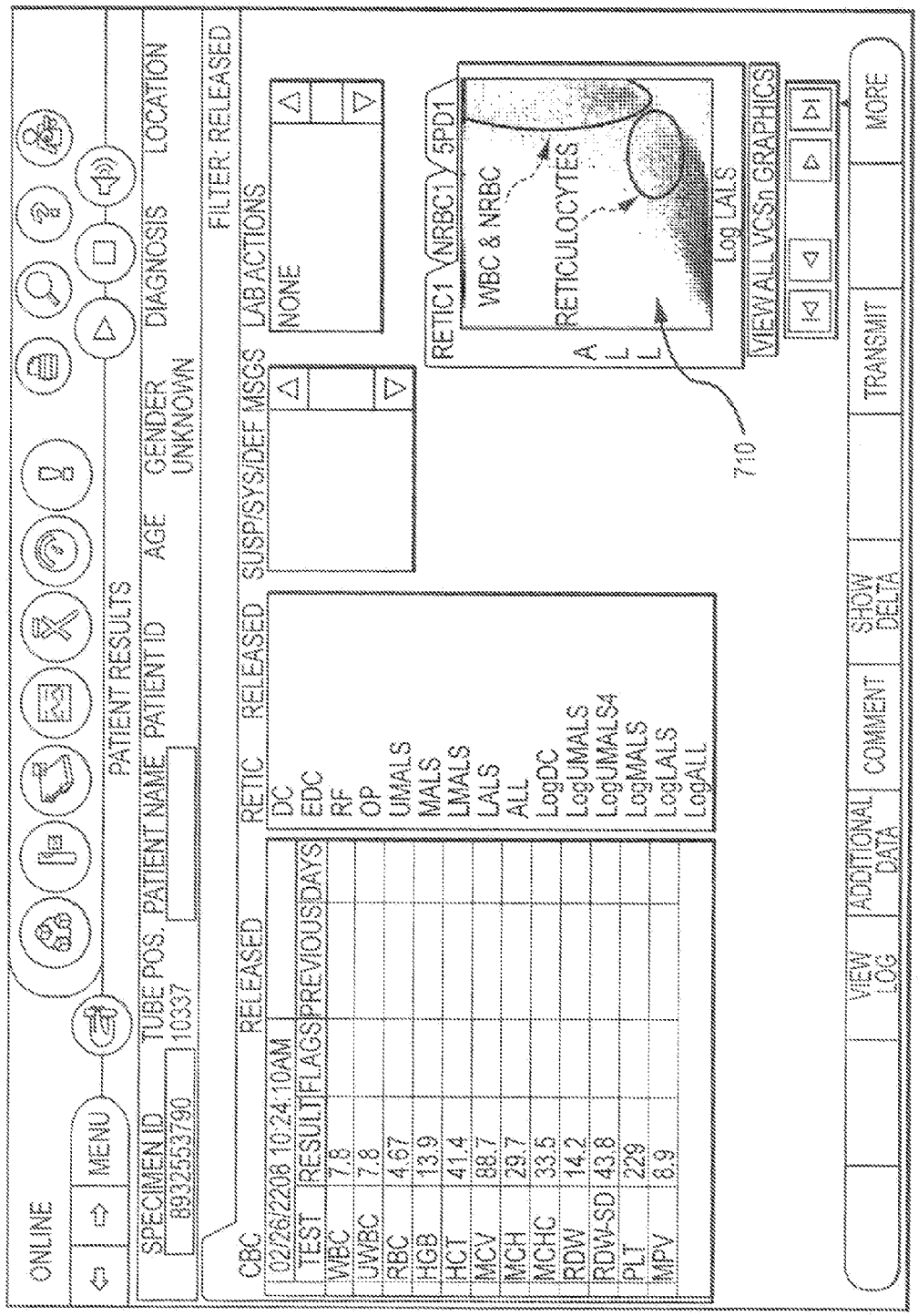
FIG. 7 depicts an exemplary screen shot of a differential count screen, according to embodiments of the present invention.

Subpopulations of cells can be separated into different groups at different locations on the histograms. For example, white blood cells and nucleated red blood cells can be clustered in a particular region of a histogram, thus forming a cell population which is distinct from another cell population such as a reticulocyte population which may be clustered in another region. In this way, different cell populations can be differentiated and analyzed. FIG. 7 depicts an exemplary screen shot 700 of a count analysis. As illustrated here, a population containing WBCs and NRBCs is encircled on the histogram 710. Generally, such histograms can be obtained from a reticulocyte channel (or a WBC differential channel or an NRBC channel) as discussed elsewhere herein.

Figure 7A:
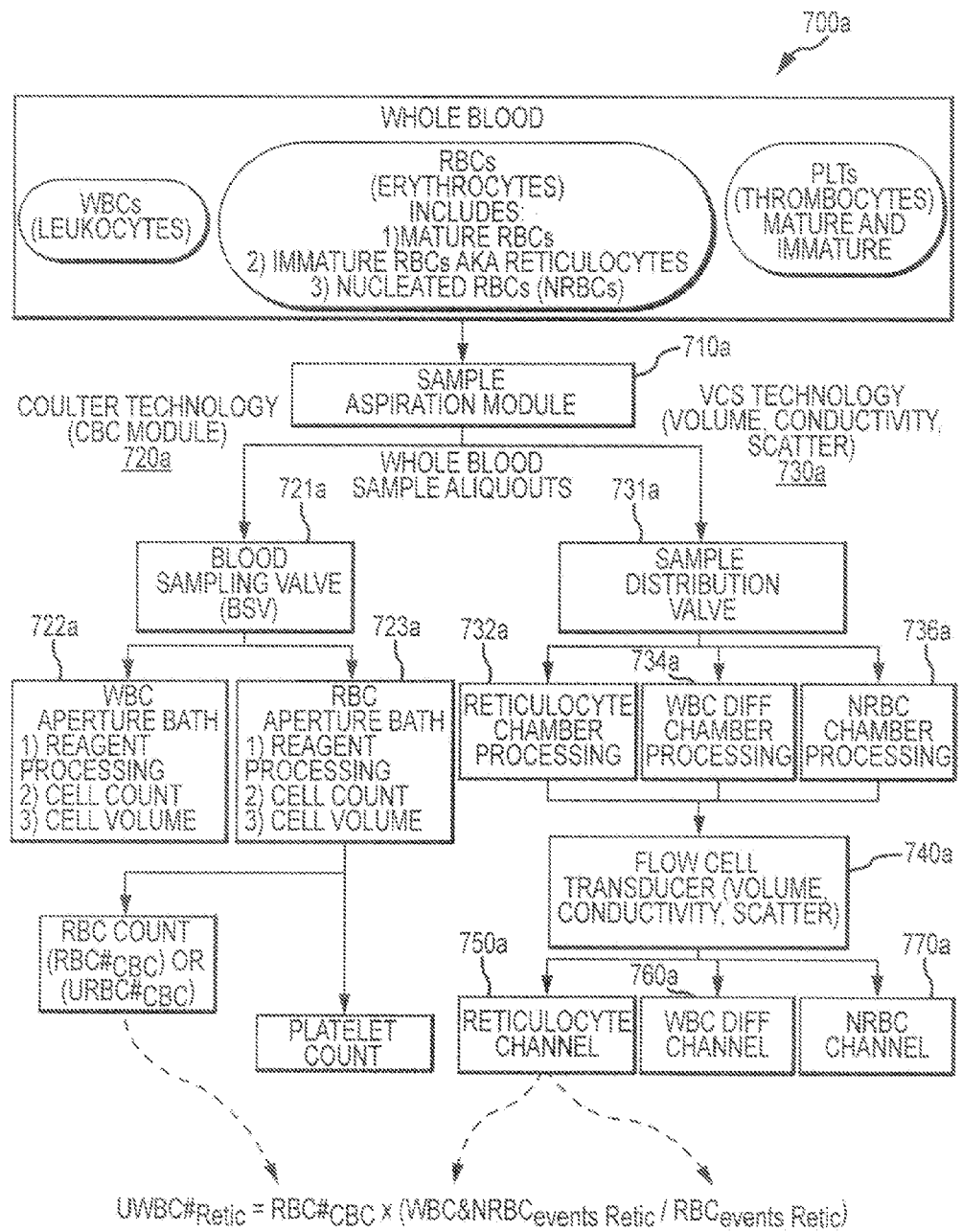
FIG. 7A schematically shows a technique for obtaining blood cell parameters, according to embodiments of the present invention.
Figure 7B:
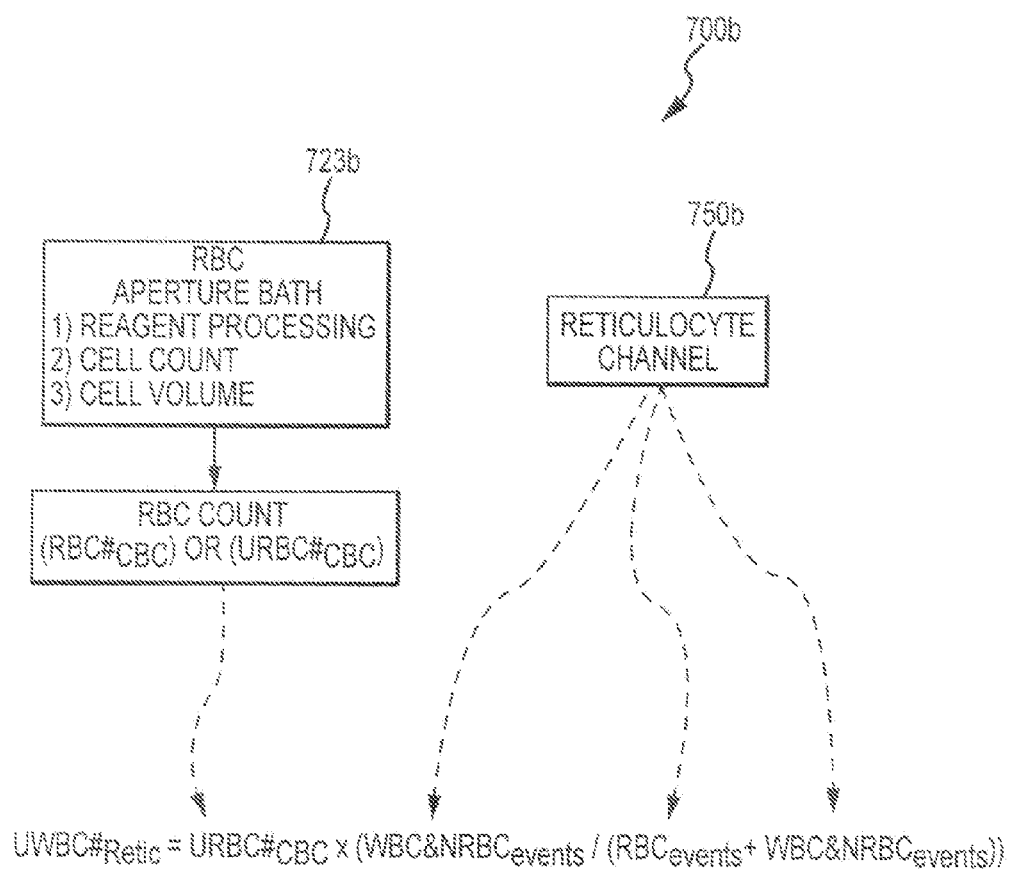
FIG. 7B schematically shows a technique for obtaining blood cell parameters, according to embodiments of the present invention.

Such VCS values can correspond to the position of the population in the histogram, and to the morphology of the blood cells under the microscope. As depicted in FIGS. 7A and 7B, certain channel modules can provide measurements for various blood components, such as blood cells or cellular debris which may be present.

VCS parameters can be used to analyze cellular events in a quantitative, objective, and automated manner, free from the subjectivity of human interpretation, which is also very time consuming, expensive, and has limited reproducibility. VCS parameters can be used in the diagnosis of various medical conditions that alter the WBC counts. It is understood that when referring to VCS parameters or volume conductivity scatter data profiles, such characterizations may include a subset of the individual VCS data features. For example, VCS parameter data may include a combination of volume and conductivity measures, a combination of volume and scatter measures, or a combination of conductivity and scatter measures. Similarly, VCS parameter data may include a volume measure only, a conductivity measure only, or a scatter measure only. In some instances, VCS parameter data may be considered to include a set or subset of light propagation and current data. For example, the light propagation measures may include a first propagated light at a first angle, a second propagated light at a second angle different from the first angle, an axial propagated light, or any combination thereof. Relatedly, the current measures may include a low frequency current (e.g DC impedance corresponding to volume), a high frequency current (e.g. RF conductivity corresponding to internal cellular density), or a combination thereof. In this sense, VCS parameter data or volume conductivity scatter data profiles may be referred to as current light propagation parameters or data profiles.

As further discussed herein, it has been discovered that certain VCS parameter values are highly useful for assessing a WBC status in an individual. Accordingly, these parameters can be implemented in systems and methods for the diagnosis of WBC-related conditions.

FIG. 7A illustrates aspects of a biological sample analysis system 700a, according to embodiments of the present invention. As depicted here, white blood cell analysis techniques may include determining both an WBC+NRBC count and an RBC count using a VCS reticulocyte channel. Further, techniques may include determining an RBC count using an RBC aperture bath of a CBC module. What is more, techniques can include calculating an uncorrected white blood cell count (UWBC) based on the WBC+NRBC count, the reticulocyte module RBC count, and the CBC module RBC count.

As shown here, the sample analysis system 700a includes a sample aspiration module 710a, a CBC module 720a (which incorporates Coulter technology), and a VCS module 730a (which incorporates VCS technology). The CBC module 720a includes a blood sampling valve 721a, which receives sample from aspiration module 710a. Further, the CBC module 720a includes a WBC aperture bath 722a which receives sample from BSV 721a (and can be used to determine a WBC count) and an RBC aperture bath 723a which receives sample from BSV 721a (and can be used to determine an RBC count). The VCS module 730a includes a sample distribution valve 731a, which receives sample from aspiration module 710a, and which can be used to transfer sample to a reticulocyte chamber 732a for processing with a flow cell transducer 740a and analysis in a reticulocyte channel 750a. Sample distribution valve 731a can also be used to transfer sample to a WBC differential chamber 734a for processing with a flow cell transducer 740a and analysis in a WBC differential channel 760a. What is more, sample distribution valve 731a can be used to transfer sample to an NRBC chamber 736a for processing with a flow cell transducer 740a and analysis in an NRBC channel 770a.

As discussed elsewhere herein, embodiments of the present invention encompass automated systems for estimating a white blood cell (WBC) status in a biological sample, where the system includes a first analyzer module (e.g. implementing Coulter technology) configured to determine a red blood cell count of the biological sample, a second analyzer module (e.g. implementing VCS technology) configured to determine a ratio of white blood cell (WBC) to red blood cell (RBC) of the biological sample, and a data processing module configured to determine the WBC status based on the Coulter red blood cell count and the VCS ratio.

According so some embodiments, sample may or may not be lysed depending on where the sample is processed in the system. For example, in many instances, sample is lysed when processed using the WBC aperture bath 722a, the WBC differential chamber 734a, and the NRBC chamber 736a. In contrast, in many instances, sample is not lysed when processed using the RBC aperture bath 723a or the reticulocyte chamber 732a. Hence, as depicted in FIG. 7A, the uncorrected white blood cell count (UWBC) can be determined based on sample which is not lysed.

According to some embodiments, a CBC module can be used to determine both a WBC count (via a WBC aperture bath) and an RBC count (via an RBC aperture bath). The parameter from the CBC module which is used in FIG. 7A is the RBC count [$RBC\#_{CBC}$]. In other words, a WBC aperture bath of a CBC module is not required.

FIG. 7B illustrates aspects of a biological sample analysis system 700b (which may also include elements of analysis system 700a described above), according to embodiments of the present invention. As depicted here, white blood cell analysis techniques may include determining both an WBC+ NRBC count and an RBC count using a VCS reticulocyte channel 750b. Further, techniques may include determining an uncorrected RBC (URBC) count using an RBC aperture bath 723b of a CBC module. What is more, techniques can include calculating an uncorrected white blood cell count (UWBC) based on the WBC+NRBC count, the reticulocyte module RBC count, and the CBC module URBC count.

Figure 8:
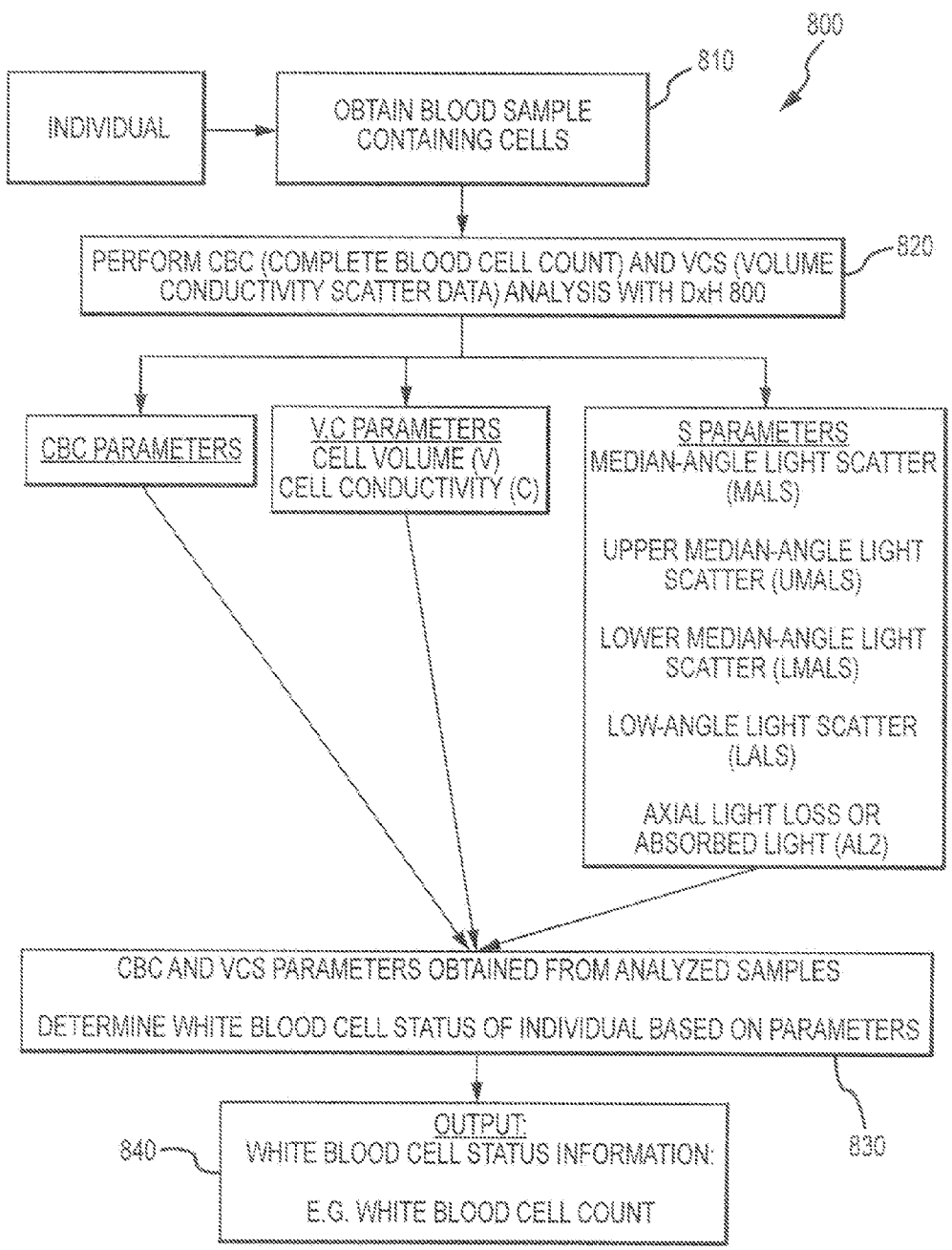
FIG. 8 illustrates aspects of a method for determining white blood cell status information based on a biological sample obtained from an individual, according to embodiments of the present invention.

FIG. 8 schematically illustrates a method 800 for obtaining a WBC parameter (e.g. count) according to embodiments of the present invention. As depicted here, the method includes obtaining blood samples from individuals (e.g. during routine examinations), as indicated by step 810. Complete Blood Count (CBC) data, Volume Conductivity Scatter (VCS) data, or combinations thereof, can be obtained from these biological samples, using a cellular analysis system that is equipped to obtain cellular event parameters, such as Beckman Coulter's UniCel® DxH 800 System, as indicated by step 820. CBC parameters, VCS parameters, or combinations thereof from analyzed samples can be used to determine the WBC parameters, as indicated by step 830. Methods may also include outputting WBC status information, as indicated in step 840.

Analysis Systems

Embodiments of the present invention encompass cellular analysis systems and other automated biological investigation devices which are programmed to carry out WBC status prediction or identification methods according to techniques as disclosed herein. For example, a system that is equipped to obtain and/or process multiple light angle detection parameters, such as Beckman Coulter's UniCel® DxH 800 System, or processors or other computer or module systems associated therewith or incorporated therein, can be configured to receive as input values for the various measurements or parameters discussed herein, and automatically output a predicted WBC status. The predicted status may provide an indication that the individual has a normal WBC level, an elevated WBC level, or a depressed WBC level, for example. In some instances, a system that is equipped to obtain and/or process multiple light angle detection parameters, such as a Beckman Coulter UniCel® DxH 800 System, may include a processor or storage medium that is configured to automatically implement a WBC count analysis, whereby data obtained from a biological sample analyzed by a system that is equipped to obtain multiple light angle detection parameters, such as the DxH 800 System, is also processed by a system that is equipped to obtain and/or process multiple light angle detection parameters, such as the DxH 800 System, and a WBC prediction or indication is provided or output by the system that is equipped to obtain and/or process multiple light angle detection parameters, such as the DxH 800 System, based on the analyzed data.

Figure 9:
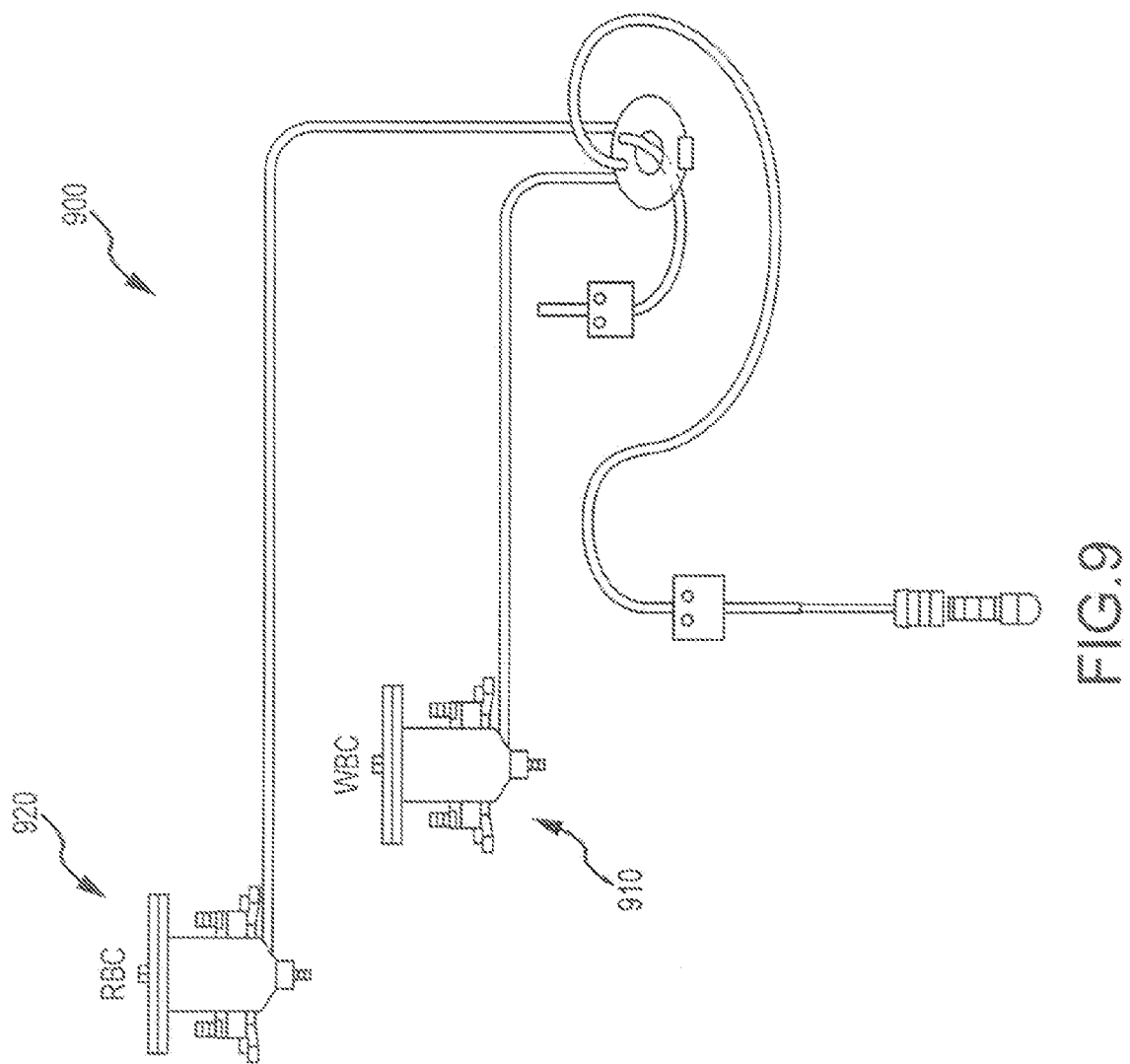
FIGS. 9 and 10 show aspects of blood cell analysis devices according to embodiments of the present invention.

FIG. 9 depicts aspects of an exemplary CBC module 900, according to embodiments of the present invention. Such CBC modules, which may be part of a system such as Beckman Coulter's UniCel® DxH 800 System, can operate to control or carry out various mechanical functions as well as electronic and photometric measurement functions for WBC, RBC and PLT cell counting and hemoglobin measurements. Exemplary CBC module can be used to prepare the samples for CBC analysis, and to generate CBC parameter measurements via aperture bath assemblies (e.g. WBC bath 910 and RBC bath 920).

Cellular elements of the blood (e.g. erythrocytes, leukocytes, and platelets) can be counted using electrical impedance methods. For example, an aspirated whole blood sample can be divided into two aliquots and mixed with an isotonic diluent. The first dilution can be delivered to the RBC aperture bath 920, and the second can be delivered to the WBC aperture bath 910. In the RBC chamber, both RBCs and platelets can be counted and discriminated by electrical impedance as the cells pass through sensing apertures. For example, particles between 2 and 20 fL can be counted as platelets, and those greater than 36 fL can be counted as RBCs. For the WBC chamber processing, an RBC-lysing reagent can be added to the WBC dilution aliquot to lyse RBCs and release hemoglobin, and then WBCs can be counted by impedance in sensing apertures of the WBC bath. In some instances, the baths may include multiple apertures. Hence, for example, a blood cell count used in a blood cell enumeration technique may be obtained using an RBC triple aperture bath.

An exemplary CBC sample preparation technique may include two processes, sample acquisition and sample delivery. Sample acquisition may occur when 165 uL of patient sample is aspirated and directed to a Blood Sampling Valve (BSV), for example as depicted in FIG. 7A. The BSV can operate to direct specific volumes of the patient sample with the DxH reagents for delivery to the two triple-aperture baths. The patient sample and the DxH reagents can be delivered to the bottom of aperture baths at an angle that, with a round design, allow the sample and reagents to thoroughly mix without mixing bubbles. The sample can then be prepared for measurement and analysis. According to some embodiments, in the WBC bath, 6.0 mL (±1.0%) of DxH diluent and 28 uL of sample can be combined with 1.08 mL (±1.0%) of DxH cell lyse for a final dilution of 1:251. According to some embodiments, in the RBC bath, 10 mL (±1.0%) of DxH diluent and 1.6 uL of sample can be combined for a final dilution of 1:6250. After the patient sample and DxH reagents are mixed, vacuum and aperture current can be applied to the apertures for the measurements of cell count and cell volume. The RBC and PLT counts can also include the application of sweep flow to prevent recirculation of cells near the aperture. In certain embodiments, data acquisition for the RBC and PLT can be up to a maximum of 20 seconds and for the WBC a maximum of 10 seconds. In certain embodiments, all analog pulses generated by the aperture assemblies can be amplified by a preamp card and then sent to a CBC signal conditioner analyzer card for analog-to-digital conversion and parameter extraction. According to some embodiments, a system such as Beckman Coulter's UniCel® DxH 800 System can be used to measure multiple parameters for each cellular event, and a digital parameter extraction process can be used to provide digital measurements such as time, volume (pulse attributes including amplitude and pulse width), count and count rate, and wait time. Such measurements can be used, optionally by a system such as Beckman Coulter's UniCel® DxH 800 System, for pulse editing, coincidence correction, count voting, generation of histograms for WBC, RBC and PLT, histogram voting, pattern analysis, and interference correction, and the like.

Figure 10:
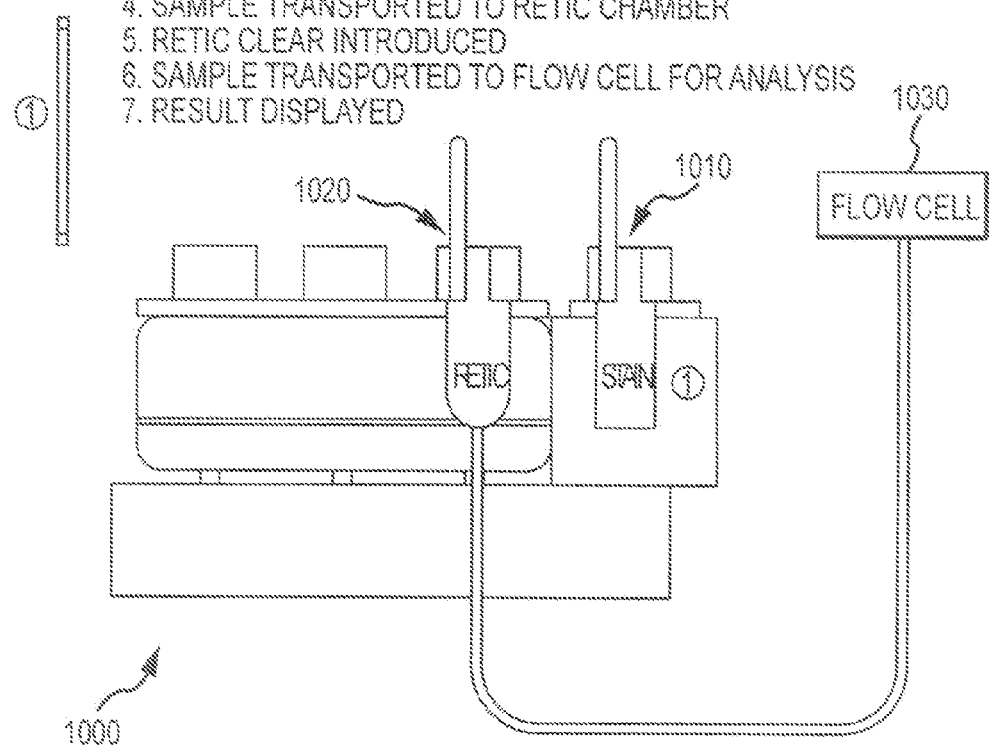

FIG. 10 depicts aspects of an exemplary reticulocyte processing chamber 1000, according to embodiments of the present invention. According to some embodiments, a reticulocyte module of a system such as Beckman Coulter's UniCel® DxH 800 can be used to apply a stain such as new methylene blue stain to a blood sample before the sample is processed through a signal-acquisition aperture (e.g. of a VCS module flow cell transducer). The new methylene blue stain is a non-fluorochrome dye that precipitates RNA of the white blood cells. The precipitated RNA can effectively increases measured light scatter signals collected at a variety of different angles. Embodiments of the present invention encompass the use of any of a variety of techniques for staining white blood cells, and materials other than or in addition to new methylene blue stain may be used. As shown here, a reticulocyte chamber and channel processing technique may include delivering an amount of blood (e.g. 27 µl) to a stain chamber 1010 [step 1], contacting the amount of blood with a stain (e.g by mixing the blood and stain) [step 2], incubating the mixture [step 3], transporting the incubated mixture to a reticulocyte chamber 1020 [step 4], introducing a retic clear reagent [step 5], transporting an amount of the sample (e.g. 4 µl) to a flow cell 1030 for analysis [step 6], and displaying the results [step 7].

Figure 10A:
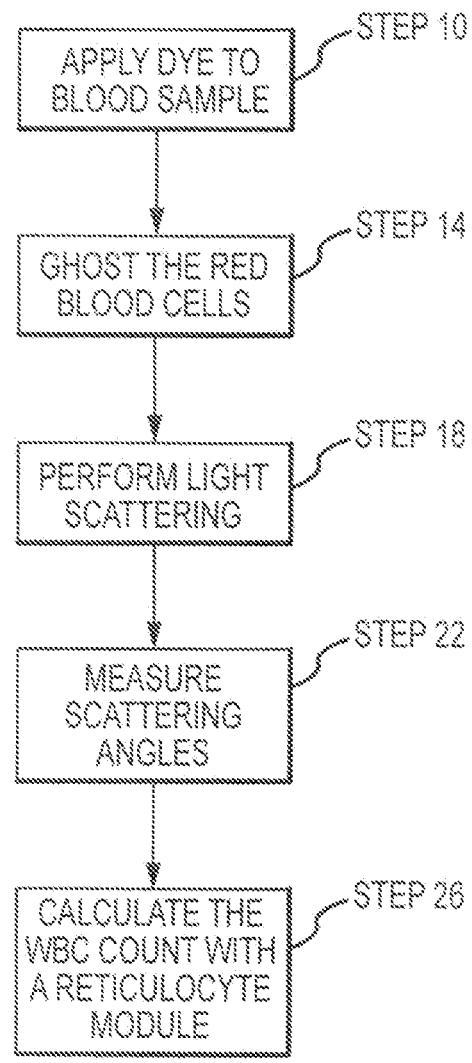
FIG. 10A illustrates aspects of blood cell analysis methods according to embodiments of the present invention.

FIG. 10A illustrates additional aspects of determining a WBC count using a reticulocyte module, according to embodiments of the present invention. As shown here, the cells of the blood sample are first incubated with a first reagent to selectively stain the ribonucleic acid of the reticulocytes (Step 10). In one embodiment the stain New Methylene Blue (NMB) is used, although any RNA specific stain can be used. Next (Step 14) the hemoglobin of the red blood cells released by a second reagent; a ghosting reagent comprising potassium thiocyanate and sulfuric acid. The ghosting reagent swells the red blood cell into a spherical shape without damaging the membrane thereby permitting the escape of hemoglobin from the red blood cell. The ghosting reagent also has a fixative property that allows the cells to maintain their spherical shape induced by the swelling caused by the ghosting agent. The resulting decrease in the hemoglobin content enhances the staining of the reticulum which permits the flow cytometric determination of the reticulocytes.

In the ghosting step the blood sample is mixed with the ghosting reagent at an elevated temperature (41° C.). The osmotic pressure of the ghosting reagent must be controlled for an effective swelling of the red cells. Osmotic pressures outside the range 75 to 110 milliosmoles can either lyse or damage the red cells or the blood cell can retain hemoglobin, preventing the differentiation of the immature reticulocytes from mature red blood cells.

The resulting dyed and ghosted sample solution is then passed through the flow cell of the hematological analyzer (Step 18) and the ALL and the scattered light is measured at various angles (Step 22). From these measurements the reticulocytes and mature RBCs may be distinguished from the white blood cells using a clustering algorithm in a reticulocyte module. From this the WBC count is correctly determined (Step 26) as discussed elsewhere herein.

Gating Techniques and Clustering

Hematology evaluations may involve simultaneous multi-parametric analysis of thousands of particles per second by suspending cells in a stream of fluid and passing them by an electronic detection apparatus. The data generated can be plotted into histograms and divided into regions. Regions are shapes that are drawn or positioned around a population of interest on a one or two parameter histogram. Exemplary region shapes include two dimensional polygons, circles, ellipses, irregular shapes, or the like. Individual events exemplified in the data correspond to unique combinations of parameters, and are accumulated in cases where multiple instances of such combinations are present. When a region is used to limit or isolate cells or events that are drawn or positioned on a histogram, such that those isolated cells or events can be manifested in a subsequent histogram, this process is referred to as gating. The data accumulated into histograms can be separated or clustered based on VCS parameters, in a series of sequential steps known as "gating" involving one or more regions. In some cases, gates are combined with each other using Boolean logic (AND, OR, NOT). A common technique involves using gates sequentially. In some cases, gates are performed in parallel.

Various manual, automated, and other gating, boundary decision, region placement, or histogram segmentation techniques may be used for segmenting or gating histogram data, and exemplary techniques are discussed in US Patent Publication No. 2010/0111400 ("Non-Linear Histogram Segmentation for Particle Analysis"), the content of which is incorporated herein by reference. For example, US 2010/0111400 describes a form of a clustering algorithm that uses a non-linear histogram segmentation for particle analysis. In general the steps performed by the algorithm include forming an initial two-dimensional histogram based on two selected parameters of the particles, in this case either the ALL and the log of the LALS or the ALL and the sum of the logs of the MALS and LALS as described elsewhere herein. Other parameters are used to separate debris and platelets from the cells of interest. The initial two-dimensional histogram is then filtered to generate a filtered two-dimensional image. The filters used are a combination of smoothing filters to remove noise and edge detection filters to attempt to find the edges of any cell populations. The result is a smoothed noise reduced image with any populations' edges detected. From this filtered two-dimensional image, a plurality of seed populations that correspond to the local amplitude maxima, are determined. Anchor points are then defined as the mid-point between pairs of the center of mass of various pairs of populations. The algorithm generates one or more linear contour lines passing through or attaching to the anchor points to separate the detected seed populations. The algorithm then adjusts the contour points to approximately minimize the energy function (f(distance, curvature, intensity)) in at least one of the linear contour lines to separate the detected seed populations. The separation of the seed populations may include expanding the contour lines to contour bands. The contour bands may then be reduced or removed by the merging of regions using a Watershed transformation. The result is that the various populations can be isolated and identified.

Table 1 provides exemplary definitions which in certain instances may be used for various parameters or terms used herein.

TABLE 1

| | |
|---|---|
| DC | DC impedance measurement |
| EDC | 2xDC |
| RF | radio-frequency impedance measurement |
| OP | the ratio of RF to DC |
| UMALS | Upper Median Angle Light Scatter |
| MALS | Median Angle Light Scatter |
| LMALS | Lower Median Angle Light Scatter |
| LALS | Low Angle Light Scatter |
| ALL | Axial Light Loss |
| LogDC | logarithmic transformation of DC |
| LogUMALS | logarithmic transformation of UMALS |

TABLE 1-continued

| | |
|---|---|
| LogUMALS4 | logarithmic transformation of UMALS over 4 decades |
| LogMALS | logarithmic transformation of MALS |
| LogLALS | logarithmic transformation of LALS |
| LogALL | logarithmic transformation of ALL |

According to some embodiments, various gating steps can be performed to obtain a WBC count. One or more of these steps can be performed based on reticulocyte module and channel processing techniques using a system such as Beckman Coulter's UniCel® DxH 800 System.

Debris Event Identification

According to some embodiments of the present invention, the histograms shown in FIGS. 11 to 18 can be based on data obtained using a reticulocyte module and channel of a cellular analysis system, such as Beckman Coulter's UniCel® DxH 800 System. As shown in FIG. 11, debris events can be detected during data acquisition. Such debris events can be identified in a LogUMALS4 vs OP view. As shown here, the debris events are located at the bottom and on the right. The identified debris events can be excluded from subsequent gating steps.

As shown in the 2D histogram here (which in some embodiments originates from gated events or in certain embodiments originates from ungated events), a region named Debris and its corresponding boundary line divides the histogram into two separate sets of events. The Debris region can be defined by the boundary line, in combination with the outer limits of the histogram boundaries (maximum OP value on the right side, minimum LogUMALS4 value on the lower side). The Debris region separates the histogram into two independent sets of data. The original data shown include all events, and the region separates the events into two separate sets, such that a first set is inside of the region (Debris) and a second set is outside of the region (NOT Debris). Hence, the region is a shape that separates the data into two subsets.

The number of gated events falling within the region boundary line (i.e. lines defining the region) can be counted or assessed. As a nonlimiting example, in some embodiments this involves determining the number of events falling within the boundary line which defines the Debris region. Further, the total number of events being analyzed can be obtained. In some embodiments this number refers to a predefined subset of all collected events. In some instances, FIG. 11 may represent a gated or an ungated histogram. The term ungated as used herein means, as a nonlimiting example, that the histogram is built using all of the data available which was obtained by the instrument.

In some embodiments the second region (NOT Debris) can be used to limit or isolate cells or events that are drawn or positioned on the histogram of FIG. 11, such that those isolated cells or events are manifested in the subsequent histogram of FIG. 12. In this way, the use of the region (NOT Debris) operates as a gating step, by limiting the number of events or cells from the first histogram (of FIG. 11) that are subsequently manifested in the second histogram (of FIG. 12). As a nonlimiting example, the region acts as a gate to filter out or isolate those events within the region boundaries, so that the events are extracted and placed in the next histogram.

The term gated as used here means, as a nonlimiting example, that the data present in the histogram is derived using a gating step, as applied to a previous histogram.

Hence, as depicted here, FIG. 11 may represent ungated or gated data, and FIG. 12 represents gated data (i.e. gated on NOT Debris events). In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data.

WBC/NRBC Event Identification

WBC and NRBC cells have a nucleus and can be identified in an ALL vs (LogMALS+LogLALS) histogram as shown in FIG. 12. The WBC/NRBC events are located in the upper right corner, which are shown as enclosed. The identified WBC/NRBC events can be excluded from subsequent gating steps.

As shown in the 2D histogram here, a region named WBC/NRBC and its corresponding boundary line divides the histogram into two separate sets of events. The WBC/NRBC region can be defined at least partially by the boundary line. The WBC/NRBC region separates the histogram into two independent sets of data, such that a first set is inside of the region (WBC/NRBC) and a second set is outside of the region (NOT WBC/NRBC). Hence, the region is a shape that separates the data into two subsets.

In some embodiments the second region (NOT WBC/NRBC) can be used to limit or isolate cells or events that are drawn or positioned on the histogram of FIG. 12, such that those isolated cells or events are manifested in the subsequent histogram of FIG. 13. In this way, the use of the region (NOT WBC/NRBC) operates as a gating step, by limiting the number of events or cells from the first histogram (of FIG. 12) that are subsequently manifested in the second histogram (of FIG. 13). As a nonlimiting example, the region acts as a gate to filter out or isolate those events within the region boundaries, so that the events are extracted and placed in the next histogram. The term gated as used here means, as a nonlimiting example, that the data present in the histogram is derived using a gating step, as applied to a previous histogram.

Hence, as depicted here, FIG. 13 represents gated data (i.e. gated on NOT WBC/NRBC events). In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data.

Platelet Event Identification

According to some embodiments, platelet events can exhibit lower DC, higher light scatters, and higher OP. One view which can be used to separate platelet events from other events is (LogDC−LogUMALS) vs (LogLALS+OP) as shown in FIG. 13. The platelet events are located in the lower right corner, which are enclosed. As shown here, the identified platelet events can be excluded (e.g. when gating on the NOT platelet events to obtain FIG. 14) or selected (e.g. when gating on the platelet events).

As shown in the 2D histogram of FIG. 13, a region named Platelet and its corresponding boundary line divides the histogram into two separate sets of events. The Platelet region can be defined at least partially by the boundary line. The Platelet region separates the histogram into two independent sets of data, such that a first set is inside of the region (Platelet) and a second set is outside of the region (NOT Platelet). Hence, the region is a shape that separates the data into two subsets.

In some embodiments the second region (NOT Platelet) can be used to limit or isolate cells or events that are drawn or positioned on the histogram of FIG. 13, such that those isolated cells or events are manifested in the subsequent histogram of FIG. 14. In this way, the use of the region (NOT Platelet) operates as a gating step, by limiting the number of events or cells from the first histogram (of FIG. 13) that are subsequently manifested in the second histogram (of FIG. 14). As a nonlimiting example, the region acts as a gate to filter out or isolate those events within the region boundaries, so that the events are extracted and placed in the next histogram. The term gated as used here means, as a nonlimiting example, that the data present in the histogram is derived using a gating step, as applied to a previous histogram.

Hence, as depicted here, FIG. 14 represents gated data (i.e. gated on NOT Platelet events). In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data.

RBC Event Identification

According to some embodiments, RBC events, including both mature RBC's and reticulocytes, can be identified in the EDC vs log ALL view as shown in FIG. 14. The RBC events are located at the lower part of the view, which are enclosed. In general, RBC events can be identified using EDC, ALL (including log ALL), scatter parameters, or combinations thereof.

Accordingly, embodiments of the present invention encompass systems and methods which can be used to identify and count blood cells events based on elevated DC, ALL, LALS, LMALS, MALS, and/or UMALS, and other parameters.

Calculating White Blood Cell Count

Embodiments of the present invention encompass systems and methods for determining a WBC count based on an WBC+NRBC count and an RBC count. As depicted in the reticulocyte channel histogram of FIG. 15, when the ALL is plotted against Log LALS, the WBC & NRBC (combined white blood cell and nucleated red blood cell) events are separated from the mature red blood cell and reticulocyte counts. In certain cases, depicted in the reticulocyte channel histogram of FIG. 16, the reticulocyte population will still overlap the WBC & NRBC population. In this case plotting the ALL against log MALS plus log LALS, as shown in the reticulocyte channel histogram of FIG. 17, leads to increased separation. Hence, adding Log MALS to Log LALS in the x-axis can improve WBC-NRBC separation for some samples.

Figure 15:
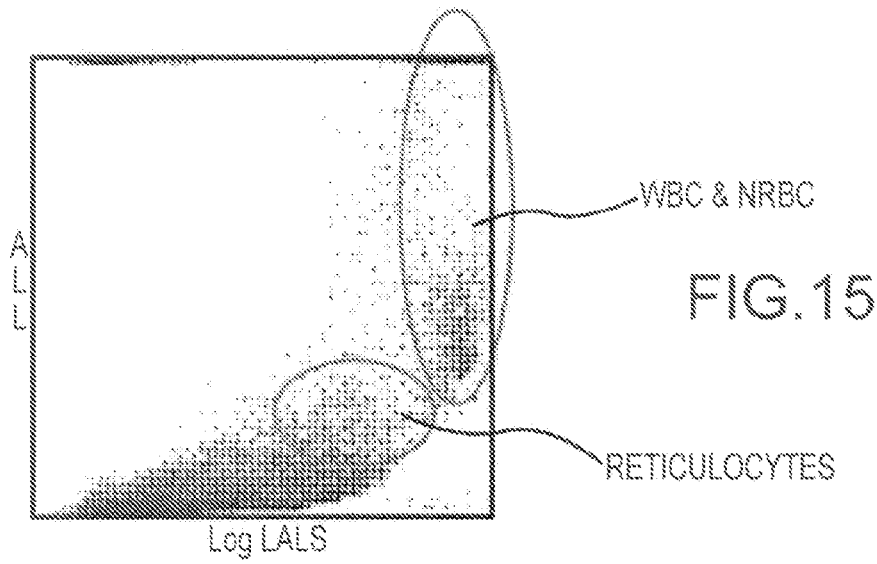
FIG. 15 depicts aspects of a gating technique according to embodiments of the present invention, and includes a plot of Axial Light Loss (ALL) versus the log of the Low Angle Light Scatter (LALS).
Figure 16:
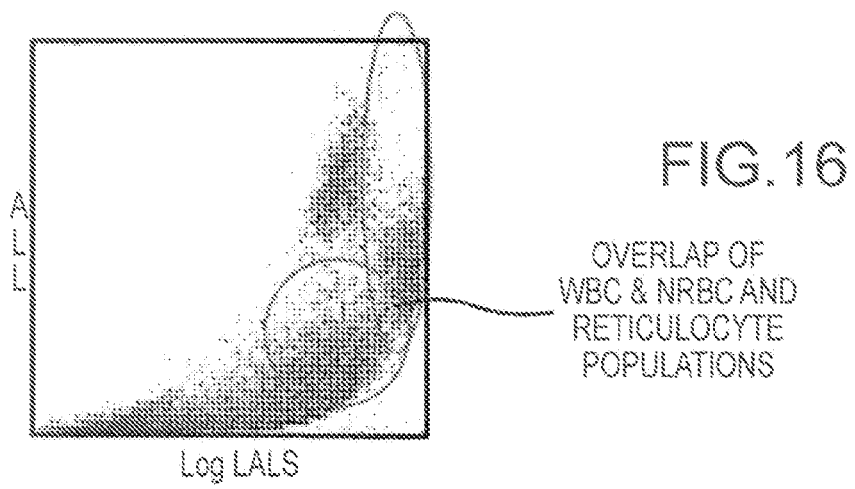
FIG. 16 depicts aspects of a gating technique according to embodiments of the present invention, and includes a plot of Axial Light Loss (ALL) versus the log of the Low Angle Light Scatter (LALS) for the case where WBCs and reticulocytes are not readily separated.
Figure 17:
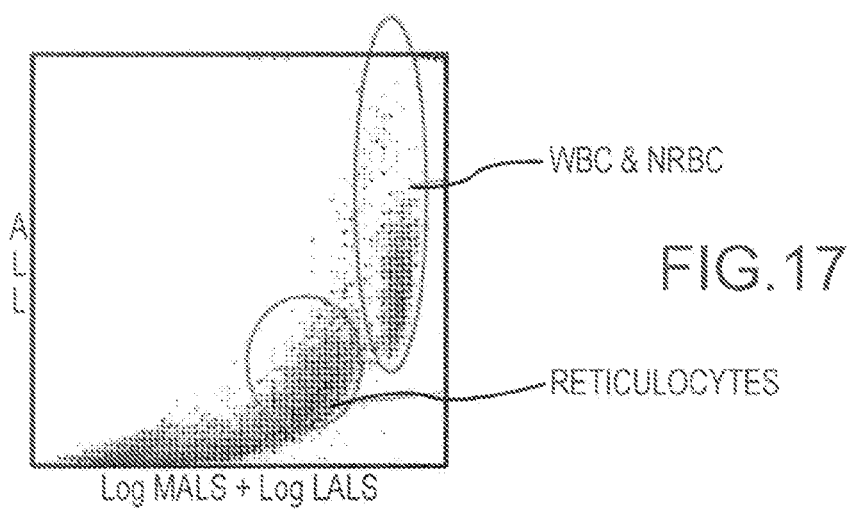
FIG. 17 depicts aspects of a gating technique according to embodiments of the present invention, and includes a plot of Axial Light Loss (ALL) versus the log of Low Angle Light Scatter (LALS) plus the log of Medium Angle Light Scatter (MALS).
Figure 18:
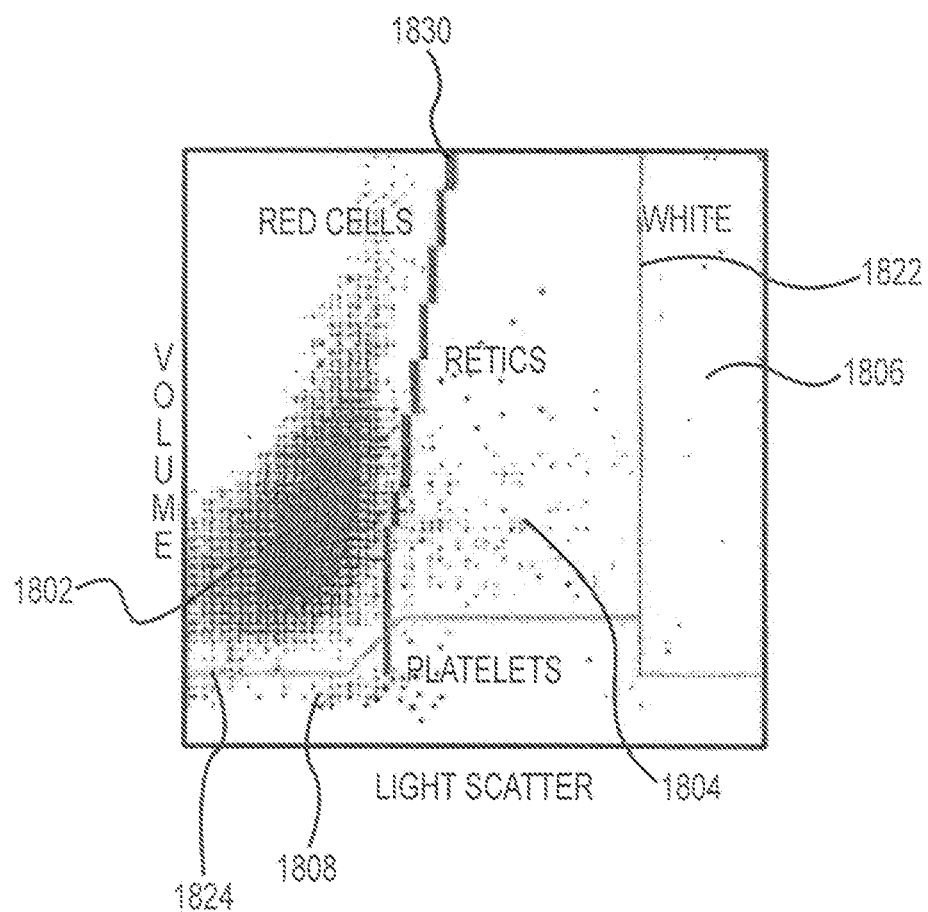
FIG. 18 depicts aspects of a gating technique according to embodiments of the present invention.

As discussed elsewhere herein, the red blood cell (RBC) event count from the reticulocyte module is useful for the WBC calculation. According to some embodiments, the RBC reticulocyte event count encompasses both mature red blood cells and reticulocytes. As depicted in FIGS. 15 to 17, various techniques can be used to determine a reticulocyte population and count. In some cases, a combined mature red blood cell and reticulocyte count is determined, without identifying reticulocytes as separate from mature red blood cells. Any of a variety of techniques may be used to determine a RBC count (e.g. combined mature red blood cells and reticulocytes) using a reticulocyte module. For example, as depicted in FIG. 18, when the Volume is plotted against a Light Scatter parameter (or a log Light Scatter parameter), mature red blood cell events 1802 and reticulocyte events 1804 can be determined. The light scatter parameter (or log thereof) can be any parameter useful for determining the RBC count. For example, the light scatter parameter can be an Upper Median Angle Light Scatter (UMALS) parameter. According to this scatter plot, event data populations of different cell types commonly found in a blood sample can be evaluated. As shown here, sufficient separation exists between the populations of red blood cells as a whole (i.e. erythrocytes 1802 and reticulocytes 1804), platelets 1808, and white blood cells 1806, that various techniques allow for gating the red cell population as a whole, for example, based on the area defined by lines 1822 and 1824. Exemplary gating techniques can involve filtering selected measurements from multi-parameter data, for example, as described elsewhere herein, separating red blood cells (erythrocytes and reticulocytes), platelets, and white blood cells by testing the measurements generated for each cell event against known threshold values. For example, line 1824 can be a threshold volume value and line 1822 can be a threshold light scatter value, where cell events with volume measurements above line 1824 and light scatter (often used in the form of log of light scatter) value less than line 1822 correspond to either erythrocytes or reticulocytes. In some cases, the reticulocyte population can also be gated, for example, by a line such as line 1830. The events to the right of line 1830 are reticulocytes, whereas the events to the left of line 1830 are mature red cells. Additional and related aspects of red blood cell analysis techniques are US Patent Publication Nos. 2010/0075369 and 2010/0240055, the contents of which are incorporated herein by reference.

In explaining various calculations used to determine a WBC count, it is helpful to define the nomenclature that is being used. In some cases, the symbol "#" designates concentration. In some cases, the subscripts "CBC", "Retic" and "NRBC" indicate the use of the standard CBC module, the Reticulocyte module, and the NRBC module respectively. The term "events" can refer to the individual particle count.

In addition to determining the WBC & NRBC counts, it is possible to calculate the WBC & NRBC to RBC counts ratio, and from that calculate the Uncorrected WBC Count (concentration) designated as (UWBC#) using the RBC count (concentration) designated as (RBC#) from the CBC module. For example, an Uncorrected WBC Count (concentration) corresponding to a reticulocyte module can be determined using the following formula:

$$UWBC\#_{Retic} = RBC\#_{CBC} \times (WBC\&NRBC_{events\ Retic} / RBC_{events\ Retic})$$

Optionally, it is possible to calculate the WBC & NRBC to RBC—plus—WBC& NRBC events ratio and also calculate the Uncorrected WBC Count (concentration) using the Uncorrected RBC count (concentration) from the CBC module. For example, an Uncorrected WBC Count (concentration) corresponding to a reticulocyte module can be determined using the following formula:

$$UWBC\#_{Retic} = URBC\#_{CBC} \times (WBC\&NRBC_{events\ Retic} / (RBC_{events\ Retic} + WBC\&NRBC_{events\ Retic}))$$

This optional approach can produce more accurate results when the WBC interference in the CBC module affects the accuracy of the RBC# count.

The Uncorrected WBC Count can be corrected by using the percentage of NRBCs (NRBC %) from the NRBC module. In some cases, an NRBC % can be determined using techniques such as those described in U.S. Pat. Nos. 7,008,792 and 7,208,319, the contents of which are incorporated herein by reference. For example, an NRBC % (which may also be referred to as an NRBC concentration) can be determined using an NRBC module as described in Example 1 of U.S. Pat. No. 7,208,319. It is noted that the term concentration as used in Example 1 of U.S. Pat. No. 7,208,319 is described as a percentage, and not as a population count in a unit of number of count per unit volume. In some cases, an NRBC % can be determined using an NRBC channel 770a as shown in FIG. 7A. As an example, a Corrected WBC Count (concentration) corresponding to a reticulocyte module can be determined using the following formula:

$$WBC\#_{Retic=UWBC\#Retic}/(1+NRBC\%_{NRBC})$$

Figure 19:
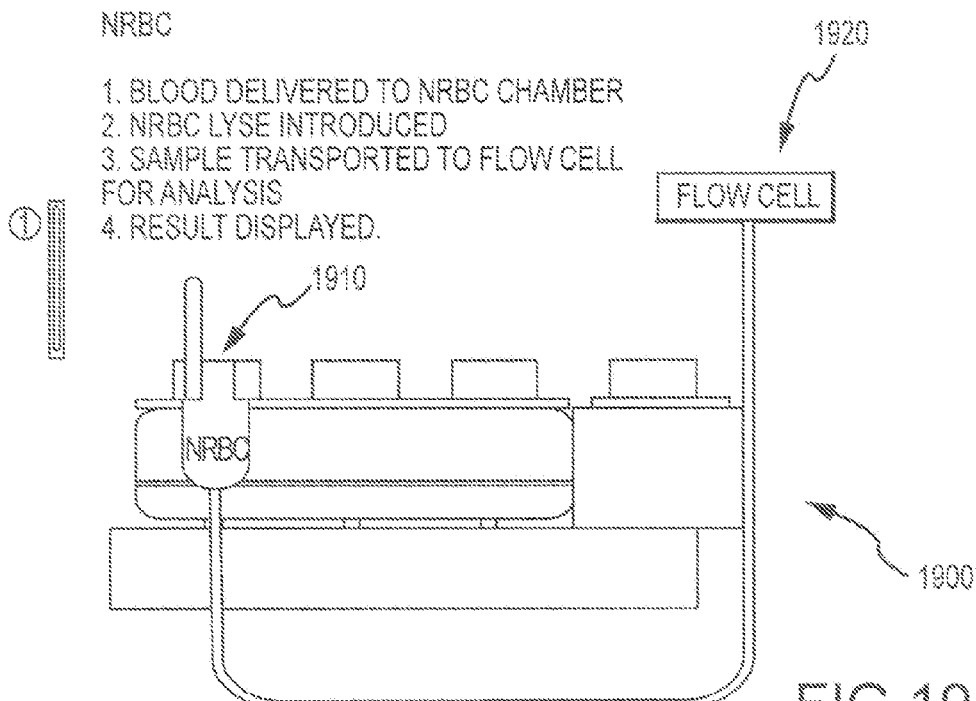
FIGS. 19 and 20 show aspects of blood cell analysis devices according to embodiments of the present invention.
Figure 20:
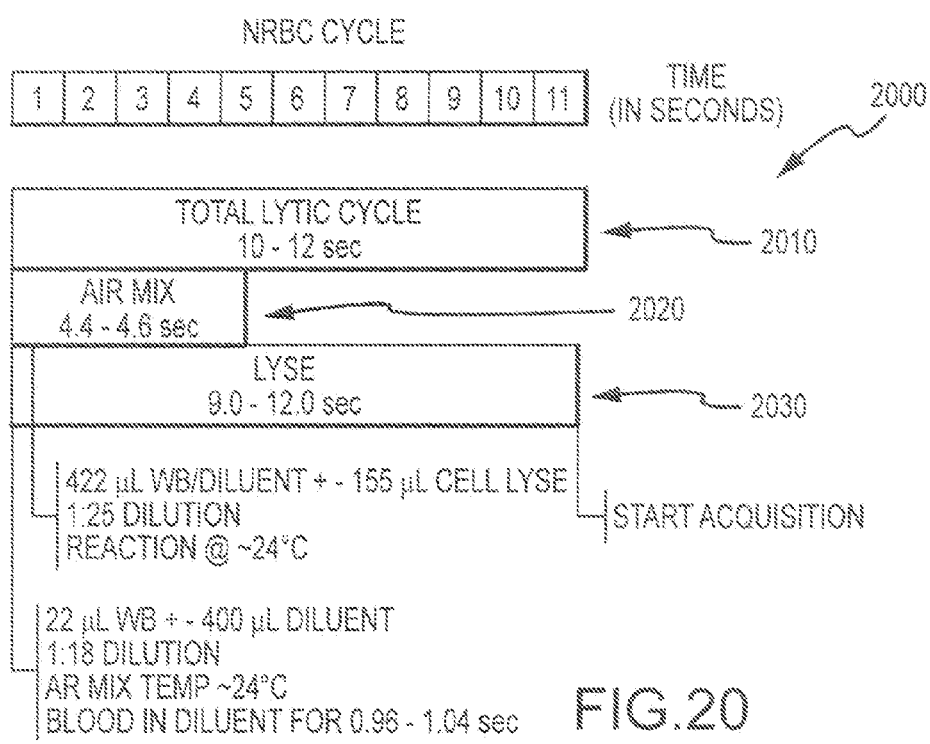

FIG. 19 depicts aspects of an exemplary NRBC processing chamber 1900, according to embodiments of the present invention. As shown here, an NRBC processing technique may include delivering blood to an NRBC chamber 1910 [step 1], and introducing an NRBC lysing agent into chamber 1910 [step 2], so as to contact the blood sample with the lysing agent. The NRBC processing technique can also include transporting the sample to a flow cell 1920 for analysis [step 3], and displaying the results [step 4]. Relatedly, FIG. 20 depicts aspects of an exemplary NRBC processing cycle, according to embodiments of the present invention. As shown here, a portion of the blood sample can be diluted and treated with a lysing reagent to selectively remove non-nucleated red blood cells while maintaining NRBCs, WBCs and any platelets or cellular debris that may be present in predictable state. An NRBC processing cycle 2000 may include a total lytic cycle 2010, an air mix cycle 2020, and a lyse cycle 2030.

Figure 21:
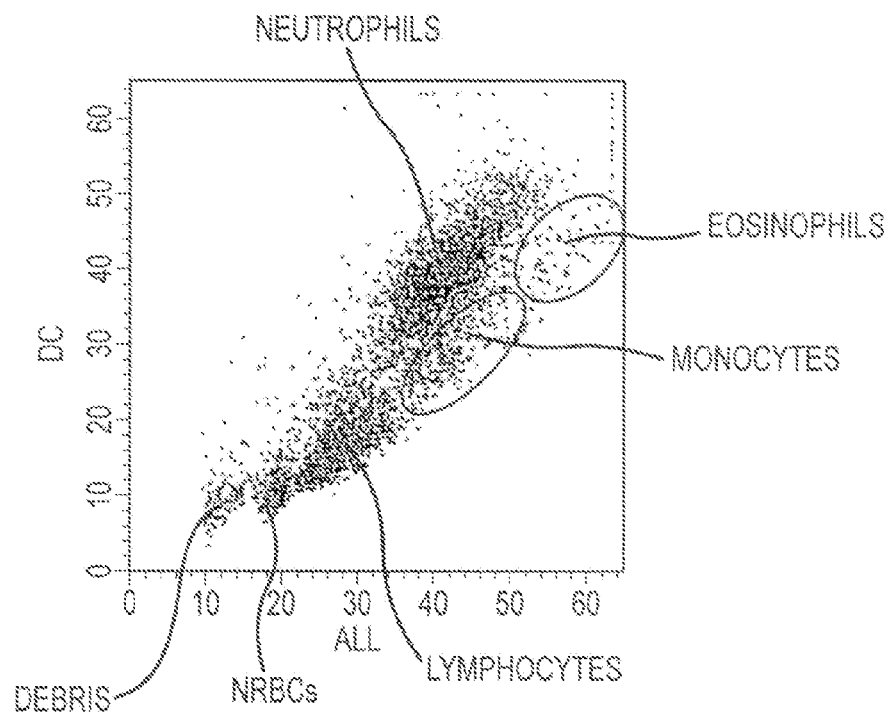
FIG. 21 is a DC vs. ALL scattergram of a clinical whole blood sample analyzed according to embodiments of the present invention.
Figure 22:
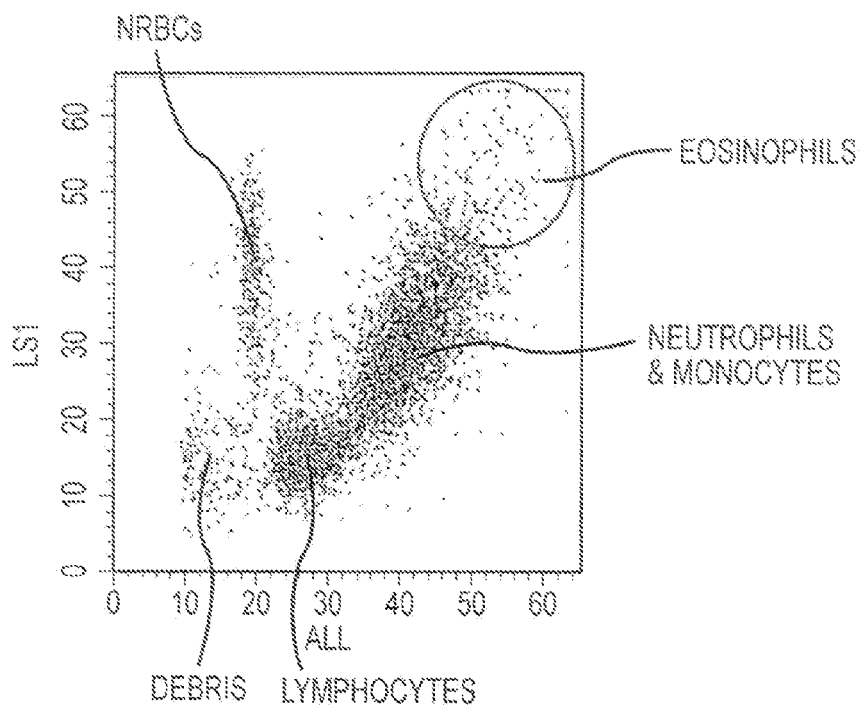
FIG. 22 is a LS1 vs. ALL scattergram of the clinical whole blood sample shown in FIG. 21.

Various Volume Conductivity Scatter (VCS) parameters can be used to analyze NRBCs using an NRBC module. In some cases, axial light loss and DC impedance measurements can be used to evaluate NRBCs. For example, FIG. 21 shows a DC vs. ALL scattergram of a clinical whole blood sample, containing nucleated red blood cells, processed and analyzed using NRBC module reagents and procedures as described elsewhere herein. As shown here, the nucleated red blood cells (NRBCs) form a cluster which is separated from white blood cells and from cell debris. The NRBC concentration of the sample can be calculated by dividing the number of cells in the identified NRBC cluster (FIG. 21) by the number of the white blood cells (WBC) and multiplying the quotient by 100. The NRBC concentration can be reported as the number of NRBC/100 WBC, which is the same as the unit of the manual reference method, or can be reported as an absolute number of NRBC per microliter ($\mu L$) of a whole blood. In another embodiment, as depicted in FIG. 22, a process for differentiating nucleated red blood cells from other cell types can use a combination of axial light loss and a low angle light scatter measurements (e.g. LS1, such as light scatter at 5.1°). In this embodiment, a lysed blood sample is analyzed in a flow cell by measuring axial light loss and low angle light scatter signals. The nucleated red blood cells are differentiated from other cell types by using the obtained axial light loss and low angle light scatter signals. In some cases, the low angle light scatter signal is measured in less than 10°. In some cases, the low angle light scatter corresponds to an angle within a range from about 1° to about 7°, or to an angle within a range from about 4° to about 6°.

In an exemplary NRBC processing technique, an amount of blood can be diluted (e.g. using an isotonic blood diluent), and mixed with an amount of a lytic reagent in a mixing chamber of a hematology analyzer. At a certain time following the mixing (e.g. about 9 seconds), the sample mixture can be delivered to a flow cell with a sheath fluid, for analysis of nucleated red blood cells. An exemplary lytic reagent can be an aqueous solution containing active components for lysing red blood cells and analysis of nucleated red blood cells, for example, 36 g/L dodecyltrimethylammonium chloride (50% solution) and 3.6 g/L tetradecyltrimethylammonium bromide, having a pH of about 4.

In another embodiment, where the WBC population does not include NRBCs, the step of counting the amount of WBCs can include simply calculating the relationship according to the following formula:

$$WBC\#_{Retic=RBC\#CBC} \times (WBC_{events\ Retic}/RBC_{events\ Retic})$$

Figure 23:
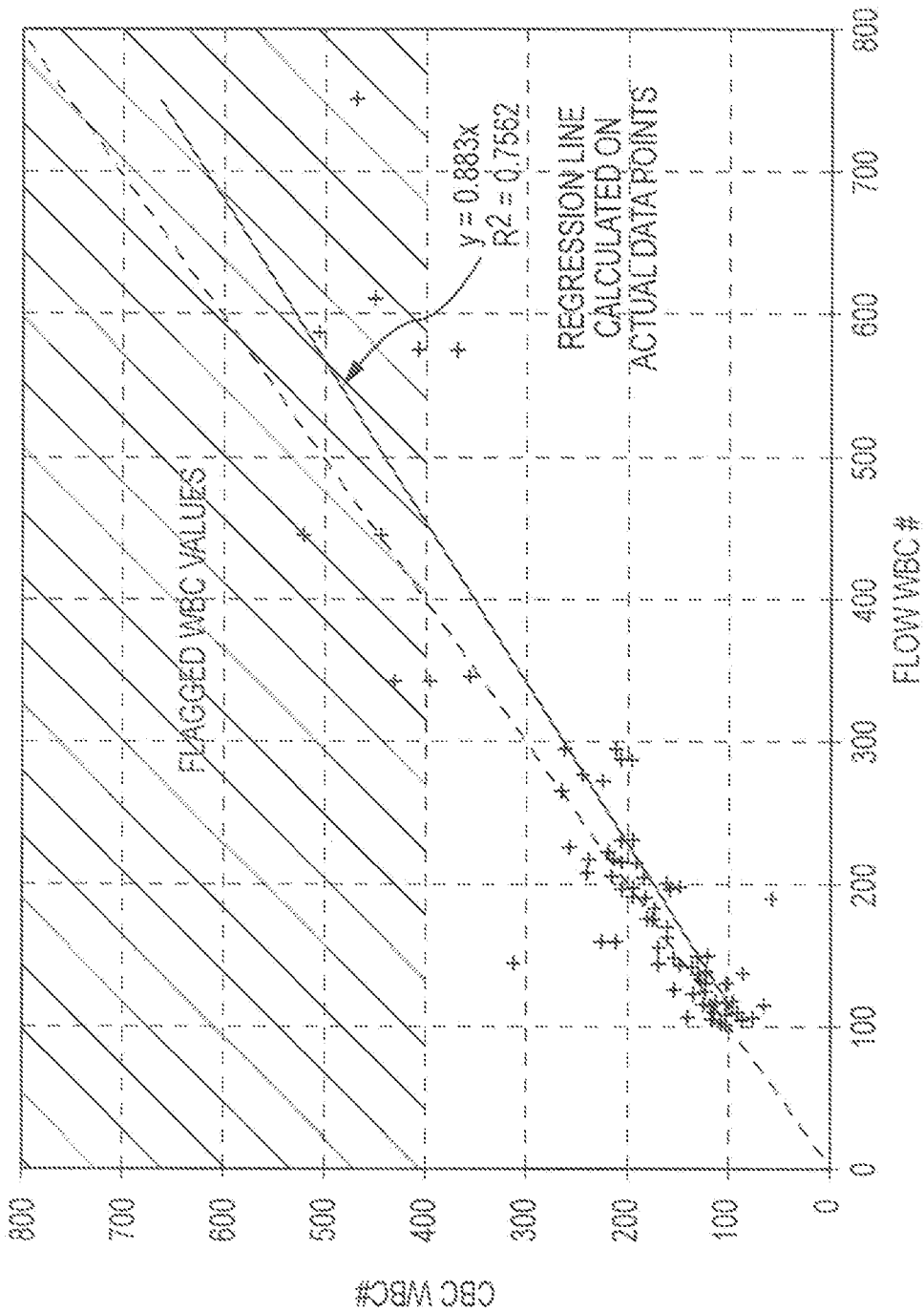
FIG. 23 depicts the relationship of the white cell count measured by a WBC module plotted against a standard.

FIG. 23 depicts the scatter of the WBC count values from a WBC module for high WBC counts plotted against a known standard. It is easily seen that for high counts of white cells, the white cell count deviates from the actual standard significantly. The regression line falls below the dotted line that represents one to one correlation. As a result the white cells are undercounted. The solid line shown here is a regression line calculated on the actual data points, and is described by the formula y=0.883x.

Figure 24:
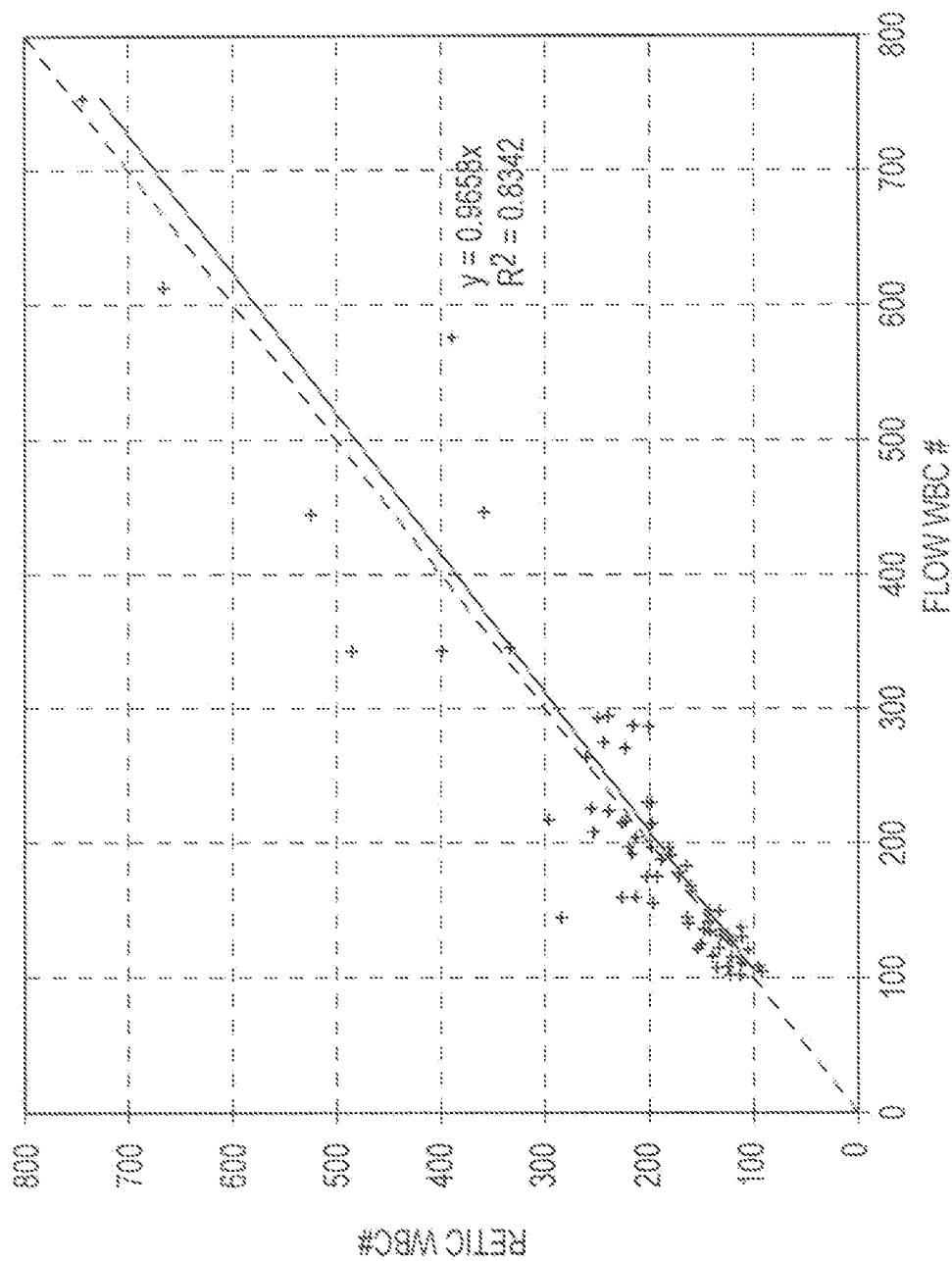
FIG. 24 depicts the relationship of the white cell count measured by a method embodiment of the present invention plotted against a standard.

FIG. 24 depicts the same measure as in FIG. 23, with the WBC count determined by the reticulocyte module being compared to a standard. As can be seen, the regression line more closely matches the dotted line that represents one to one correlation. This technique may be used with any hematology analyzer that is equipped to measure light scatter parameters (e.g. light scatter and axial light loss), as well as RBC (mature RBC and reticulocytes) and WBC & NRBC events in the same sample.

As discussed elsewhere herein, the WBC count techniques are particularly useful for analyzing samples containing high numbers of WBCs. For example, exemplary techniques can be used to produce a WBC Count for sample which exceed 400 WBC per $10^3/\mu L$. Moreover, exemplary techniques can produce a reliable WBC count even where there is interference from large platelets, platelet clumps, NRBCs, or other interferences substances such as lipids and the like.

Embodiments of the present invention provide WBC count techniques which can report a large range of WBC count values. Further, the WBC count techniques disclosed herein can be implemented without requiring compensation for a loss of WBC count due to coincidence. A reticulocyte module can process RBCs which are generally 1000 times as dense as WBCs. Hence, coincidence can be ignored for WBC counts.

As discussed elsewhere herein, exemplary WBC count techniques can be implemented without the use of lytic procedures which separate RBCs and WBCs by chemically destroying RBCs. Such lytic procedures often require precise control and dispensing protocols, special reagents, specific timing and temperature parameters, and the like. Relatedly, any unlysed RBCs can cause serious interference to WBCs. Embodiments of the present invention encompass techniques which avoid these issues, by using digital processing methods to separate RBCs from WBCs. Moreover, exemplary WBC techniques can be implemented without the use of a flow rate measurement or control (e.g. which are often used in calculating sample volume). Further, exemplary WBC techniques can operate to separate WBCs from platelet interference in a multi-dimensional space, and hence can avoid issues associated with giant platelet or platelet clump interference.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

It is to be understood that the figures and descriptions of embodiments of the invention have been simplified to illustrate elements that are relevant for a clear understanding of the invention. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. An automated system for determining a white blood cell status in a biological sample, the system comprising:
   a first module configured to determine a first red blood cell concentration of the biological sample;
   a second module configured to determine a combined white blood cell and nucleated red blood cell concentration of the biological sample, and a second red blood cell concentration of the biological sample, and
   a data processing module in connectivity with the first and second modules, the data processing module comprising a processor and a tangible non-transitory computer readable medium, the computer readable medium programmed with a computer application that, when executed by the processor, causes the processor to determine the white blood cell status based on a multiplication product of a first factor and a second factor, the first factor comprising the first red blood cell concentration determined by the first module and the second factor comprising a ratio of the combined white blood cell and nucleated red blood cell concentration determined by the second module to the second red blood cell concentration determined by the second module.

2. The system according to claim 1, wherein the biological sample is unlysed.

3. The system according to claim 1, wherein the first red blood cell concentration is a total red blood cell concentration, the total red blood cell concentration comprising a combined mature red blood cell and reticulocyte concentration.

4. The system according to claim 1, further comprising a third module configured to determine a nucleated red blood cell percentage of the biological sample, wherein the computer application of the data processing module, when executed by the processor, causes the processor to determine an adjusted white blood cell status based on the first red blood cell concentration, the combined white blood cell and nucleated red blood cell concentration, the second red blood cell concentration, and the nucleated red blood cell percentage.

5. The system according to claim 4, wherein the adjusted white blood cell status is based on a ratio of the white blood cell status to the nucleated red blood cell percentage of the biological sample.

6. The system according to claim 1, wherein the second module is further configured to determine an estimated white blood cell concentration of the biological sample, and wherein the computer application of the data processing module, when executed by the processor, causes the processor to determine an adjusted white blood cell status based on a multiplication product of the first red blood cell concentration and a ratio of the estimated white blood cell concentration to the second red blood cell concentration.

7. The system according to claim 1, further comprising:
(a) an optical element having a cell interrogation zone;
(b) a flow path configured to deliver a hydrodynamically focused stream of the biological sample toward the cell interrogation zone;
(c) an electrode assembly configured to measure direct current (DC) impedance of cells of the biological sample passing individually through the cell interrogation zone;
(d) a light source oriented to direct a light beam along a beam axis to irradiate the cells of the biological sample individually passing through the cell interrogation zone;
(e) a light detection assembly optically coupled to the cell interrogation zone so as to measure light scattered by and transmitted through the irradiated cells of the biological sample, the light detection assembly configured to measure:
  (i) a first propagated light from the irradiated cells within a first range of relative to the light beam axis;
  (ii) a second propagated light from the irradiated cells within a second range of angles relative to the light beam axis, the second range being different than the first range; and
  (iii) an axial light propagated from the irradiated cells along the beam axis; and
(f) an aperture bath configured to determine the first red blood cell concentration of the biological sample;
wherein the computer application of the data processing module, when executed by the processor, causes the processor to correlate a first subset of the DC impedance, the first propagated light, the second propagated light, and the axial light measurements from the cells of the biological sample to determine the combined white blood cell and nucleated red blood cell concentration, and
wherein the computer application of the data processing module, when executed by the processor, causes the processor to correlate a second subset of the DC impedance, the first propagated light, the second propagated light, and the axial light measurements from the cells of the biological sample to determine the second red blood cell concentration.

8. The system according to claim 7, wherein the first subset comprises the first propagated light and the axial light measurements, the first propagated light measurement comprising a low angle light scatter (LALS) measurement and the axial light measurement comprising an axial light loss (ALL) measurement.

9. The system according to claim 7, wherein the second subset comprises the DC impedance and the first propagated light measurements.

10. The system according to claim 1, wherein the determination of the white blood cell status comprises a determination of white blood cell concentration.

11. The system according to claim 10, wherein the computer application of the data processing module, when executed by the processor, causes the processor to determine the white blood cell concentration as a count of white blood cells per volume of blood.

12. The system according to claim 1, further comprising an output device that outputs the white blood cell status from the data processing module.

13. The system according to claim 1, wherein the computer application of the data processing module, when executed by the processor, causes the processor to generate a report comprising the white blood cell status.

14. An automated method for determining a white blood cell status in a biological sample, the method comprising:

determining, using a first module, a first red blood cell concentration of the biological sample;
determining, using a second module, a combined white blood cell and nucleated red blood cell concentration of the biological sample, and a second red blood cell concentration of the biological sample, and
determining, using a data processing module, the white blood cell status,
wherein the data processing module comprises a processor and a tangible non-transitory computer readable medium, and the computer readable medium is programmed with a computer application that, when executed by the processor, causes the processor to determine the white blood cell status based on a multiplication product of a first factor and a second factor, the first factor comprising the first red blood cell concentration and the second factor comprising a ratio of the combined white blood cell and nucleated red blood cell concentration to the second red blood cell concentration.

15. The method according to claim 14, wherein the biological sample is unlysed.

16. The method according to claim 14, wherein the first red blood cell concentration is a total red blood cell concentration, the total red blood cell concentration comprising a combined mature red blood cell and reticulocyte concentration.

17. The method according to claim 14, further comprising determining, using a third module, a nucleated red blood cell percentage of the biological sample, wherein the step of determining the white blood cell status comprises determining an adjusted white blood cell status based on the first red blood cell concentration, the combined white blood cell and nucleated red blood cell concentration, the second red blood cell concentration, and the nucleated red blood cell percentage.

18. The method according to claim 17, wherein the adjusted white blood cell status is determined based on a ratio of the white blood cell status to the nucleated red blood cell percentage of the biological sample.

19. The method according to claim 14, further comprising determining, using the second module, an estimated white blood cell concentration of the biological sample, wherein the computer application of the data processing module, when executed by the processor, causes the processor to determine an adjusted white blood cell status based on a multiplication product of the first red blood cell concentration and a ratio of the estimated white blood cell concentration to the second red blood cell concentration.

20. The method according to claim 14, further comprising:
(a) delivering a hydrodynamically focused stream of the biological sample toward a cell interrogation zone of an optical element;
(b) measuring, with an electrode assembly, current (DC) impedance of cells of the biological sample passing individually through the cell interrogation zone;
(c) irradiating, with an electromagnetic beam having an axis, cells of the biological sample individually passing through the cell interrogation zone;
(d) measuring, with a light detection assembly, a first propagated light from the irradiated cells within a first range of relative to the beam axis;
(e) measuring, with the light detection assembly, a second propagated light from the irradiated cells within a second range of angles relative to the beam axis, the second range being different than the first range; and
(f) measuring, with the light detection assembly, axial light propagated from the irradiated cells along the beam axis;

wherein the second module determines the combined white blood cell and nucleated red blood cell concentration based on a first subset of DC impedance, the first propagated light, the second propagated light, and the axial light measurements from the cells of the biological sample, and wherein the second module determines the second red blood cell concentration based on a second subset of DC impedance, the first propagated light, the second propagated light, and the axial light measurements from the cells of the biological sample.

21. The method according to claim 20, wherein the first subset comprises the first propagated light and the axial light measurements, the first propagated light measurement comprising a low angle light scatter (LALS) measurement and the axial light measurement comprising an axial light loss (ALL) measurement.

22. The method according to claim 20, wherein the second subset comprises the DC impedance and the first propagated light measurements.

23. The method according to claim 14, wherein the step of determining the white blood cell status comprises determining the white blood cell concentration.

24. The method according to claim 14, wherein the computer application of the data processing module, when executed by the processor, causes the processor to determine a white blood cell concentration as a count of white blood cells per volume of blood.

25. The method according to claim 14, further comprising outputting, from the data processing module, the white blood cell status.

26. The method according to claim 14, further comprising generating, with the processor, a report comprising the white blood cell status.

* * * * *